United States Patent
Notz et al.

(10) Patent No.: US 10,566,078 B1
(45) Date of Patent: Feb. 18, 2020

(54) METHOD OF DETERMINATION OF OPERATING AND/OR DIMENSIONING PARAMETERS OF A GAS TREATMENT PLANT

(71) Applicant: BASF SE, Ludwigshafen (DE)

(72) Inventors: Ralf Notz, Ludwigshafen (DE); Agnes Dittel, Ludwigshafen (DE); Georg Sieder, Ludwigshafen (DE); Torsten Katz, Ludwigshafen (DE); Gustavo Adolfo Lozano Martinez, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/135,494

(22) Filed: Sep. 19, 2018

(51) Int. Cl.
G06F 17/12 (2006.01)
G06N 7/00 (2006.01)
G16C 20/10 (2019.01)
B01D 53/14 (2006.01)
G16C 20/30 (2019.01)

(52) U.S. Cl.
CPC ......... G16C 20/10 (2019.02); B01D 53/1412 (2013.01); G06F 17/12 (2013.01); G06N 7/00 (2013.01); G16C 20/30 (2019.02); B01D 2252/20421 (2013.01); B01D 2252/20426 (2013.01); B01D 2252/20431 (2013.01)

(58) Field of Classification Search
None
See application file for complete search history.

(56) References Cited

U.S. PATENT DOCUMENTS

| | | | |
|---|---|---|---|
| 7,367,018 | B2 | 4/2008 | Noble et al. |
| 8,650,013 | B2 | 2/2014 | Hanley |
| 8,983,815 | B2 | 3/2015 | Bleackley et al. |
| 9,095,785 | B2 | 8/2015 | Hanley |
| 9,534,464 | B1 | 1/2017 | Kelley et al. |
| 2002/0013000 | A1 | 1/2002 | Fagrell et al. |
| 2003/0097243 | A1 | 5/2003 | Mays et al. |

(Continued)

FOREIGN PATENT DOCUMENTS

| | | |
|---|---|---|
| EP | 2821121 | 1/2015 |
| WO | 2011062710 | 5/2011 |

(Continued)

OTHER PUBLICATIONS

Adib, H., Sharifi, F., Mehranbod, N., Kazerooni, N. M., & Koolivand, M. (2013). Support Vector Machine based modeling of an industrial natural gas sweetening plant. Journal of Natural Gas Science and Engineering, 14, 121-131. (Year: 2013).*

(Continued)

*Primary Examiner* — Bijan Mapar
(74) *Attorney, Agent, or Firm* — Lowenstein Sandler LLP

(57) ABSTRACT

The present invention relates to methods and systems for determining operating and/or dimensioning parameters of a gas treatment plant including at least one gas treatment unit as well as methods and units for generating a request to initiate the determination of operating and/or dimensioning parameters of a gas treatment plant. The present invention further relates to a computer program and non-volatile or non-transitory storage medium with the computer program, which when executed on one or more processors, performs one or more of the methods.

20 Claims, 8 Drawing Sheets

(56) References Cited

U.S. PATENT DOCUMENTS

| | | | |
|---|---|---|---|
| 2008/0125881 | A1 | 5/2008 | Grott et al. |
| 2011/0245937 | A1 | 10/2011 | Rawson et al. |
| 2013/0144591 | A1 | 6/2013 | Khan |
| 2014/0330542 | A1 | 11/2014 | Subramanian et al. |
| 2015/0134317 | A1 | 5/2015 | Maturana |
| 2017/0064900 | A1 | 3/2017 | Zemenchik |
| 2017/0236067 | A1 | 8/2017 | Tjiong |
| 2018/0311609 | A1* | 11/2018 | McCool ............ B01D 53/0454 |

FOREIGN PATENT DOCUMENTS

| | | |
|---|---|---|
| WO | 2011133805 A2 | 10/2011 |
| WO | 2014032113 | 3/2014 |
| WO | 2018146233 | 8/2018 |
| WO | 2018210738 | 11/2018 |

OTHER PUBLICATIONS

Kale, Chinmay, Andrzej Górak, and Hartmut Schoenmakers. "Modelling of the reactive absorption of CO2 using mono-ethanolamine." International Journal of Greenhouse Gas Control 17 (2013): 294-308. (Year: 2013).*

Mores, P., Rodriguez, N., Scenna, N., & Mussati, S. (2012). CO2 capture in power plants: Minimization of the investment and operating cost of the post-combustion process using MEA aqueous solution. International Journal of Greenhouse Gas Control, 10, 148-163. (Year: 2012).*

Selvan, K. K., & Panda, R. C. (2018). Mathematical Modeling, Parametric Estimation, and Operational Control for Natural Gas Sweetening Processes. ChemBioEng Reviews, 5(1), 57-74. (Year: 2018).*

Goedecke, Ralf, "Fluidverfahrenstechnik: Grundlagen, Methodik, Technik, Praxis", 2011, Wiley-VCH Verlag GmbH, Germany, 4 pages.

European Search Report for EP Patent Application No. 18195373.8, dated Apr. 12, 2019, 4 pages.

Garcia, et al., "ASPEN PLUS simulation model for CO2 removal with MEA: Validation of desorption model with experimental data", Journal of Environmental Chemical Engineering, vol. 5, Issue 5, Oct. 2017, pp. 4693-4701.

Kishimoto, et al., "Exergy recuperative CO2 gas separation in pre-combustion capture", Clean Technologies and Environmental Policy, vol. 14, Issue 3, Jun. 2012, pp. 465-474.

Zhang, et al., "Modeling CO2 Absorption and Desorption by Aqueous Monoethanolamine Solution with Aspen Rate-based Model", Energy Procedia, vol. 37, 2013, pp. 1584-1596.

* cited by examiner

200

| Inlet Stream 210<br>Solvent 220<br>Configuration<br>Units<br>  Absorber 230<br>  Flash<br>  Regenerator<br>  Heat Exchangers | Absorber<br>240 |
|---|---|
| | ☒Packing ☐ Tray<br><br>Number of segments   Pressure drop   Packing type<br>.....                      ...                        ... |
| | ☒  Hydraulic load ☐Diameter   250<br>....<br><br>☒  Solution temperature ☐Temperature difference<br>     (in-out) ☐Transferred heat<br>                                             260<br>....<br><br>☒  Concentration CO2 at aborber top ☐Absorber<br>     height<br>                                             270<br>....<br><br>☒  Loading factor at absorber bottom ☐Maximum<br>     loading factor ☐ Flow rate   280<br>.... |

Fig. 5

METHOD OF DETERMINATION OF OPERATING AND/OR DIMENSIONING PARAMETERS OF A GAS TREATMENT PLANT

TECHNICAL FIELD

The present invention relates to methods and systems for determining operating and/or dimensioning parameters of a gas treatment plant including at least one gas treatment unit as well as methods and units for generating a request to initiate the determination of operating and/or dimensioning parameters of a gas treatment plant. The present invention further relates to a computer program and non-volatile or non-transitory storage medium with the computer program, which when executed on one or more processors, performs one or more of the methods.

BACKGROUND

Gas treatment plants are typically used in large-scale plants like oil and gas facilities, gas cleaning plants, carbon dioxide capture facilities, liquefied natural gas (LNG) plants, oil refineries, petrochemical facilities or chemical facilities. In such large-scale plants fluid streams occur which contain acid gases such as $CO_2$, $H_2S$, $SO_2$, $CS_2$, HCN, COS or mercaptans. These fluid streams can be, for example, gas streams (such as natural gas, synthesis gas or heavy oil or heavy residues, coke-oven off-gases, refinery gas or reaction gases formed in the partial oxidation of organic materials, for example coal or mineral oil) or liquid or liquefied hydrocarbon streams, such as LPG (liquefied petroleum gas) or NGL (natural gas liquids). The removal of the acid gases from these fluid streams is desirable for various reasons.

Before these fluids can be transported or further processed, the acid gas content of the fluids must be markedly reduced. $CO_2$, for example, must be removed from natural gas, since a high concentration of $CO_2$ reduces the calorific value of the gas. Furthermore, $CO_2$, in combination with the water frequently entrained in fluid streams can lead to corrosion on pipes and fittings.

The removal of sulfur compounds from these fluid streams is important for various reasons. For example, the sulfur compound content of natural gas must be reduced by suitable treatment measures immediately at the natural gas source, since the sulfur compounds, together with the water frequently entrained by natural gas, also form acids which act corrosively.

For the transport of the natural gas in a pipeline, therefore preset limit values of the sulfurous impurities must not be exceeded. Furthermore, numerous sulfur compounds, even at low concentrations, are foul-smelling, and, in particular hydrogen sulfide, toxic.

In this area companies need to make major multi-million-dollar investment decisions about the most appropriate capacity and functionality of the facility. Since there are many potential configuration and design options for the gas treatment plants, it is difficult to identify viable options and to select the optimal gas treatment plant design. Therefore, a design process is followed to find an optimal gas treatment plant design for given conditions. The design is then implemented in the physical gas treatment plant. Such design processes are highly complex technical tasks, since the envisaged operation of the gas treatment plant with multiple gas treatment units depends on various parameters such as the inlet stream composition, the treatment solution properties, dimensions of the gas treatment units or the thermodynamic environment in gas treatment units. Correlations between these parameters further increase the complexity. As a result, present design methods require a large amount of input data to create viable results reflecting the physical gas treatment plants operation and output properties.

EP 2 534 592 A2 describes methods and compositions computer modeling apparatuses including an input unit enabling user specification of a subject facility design based on limited data. The subject facility design includes design alternatives, and a processor routine coupled to the input unit and responsive to the user specification by forming an input data set to a rigorous simulation modeler to model the subject facility design. The rigorous simulation modeler requires input beyond the limited data.

One problem arising when using such applications is that the user needs to define several input parameters including correlated input parameters. Based on these specifications the composition of the treated outlet gas is calculated. For achieving a specified composition in the treated outlet gas, the designer needs to manually change input parameters. In addition, the complex calculation can easily lead to undesirable and/or physically not meaningful process conditions and unreasonable designs. Such conditions can even lead to non-convergence of the calculation, which in turn leads to a lot of manual and time-consuming iteration steps, which make the design process very tedious and inefficient.

Accordingly, it is an object of the present invention to provide an improved process for designing gas treatment plants, which leads to a significant simplification of the process, reduces the burden on the user and allows to streamline and accelerate the process of implementing gas treatment plants.

SUMMARY

The present invention relates to a method, particularly a computer-implemented method, for determining operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the method may be carried out by a computer or a distributed computer system, the method comprising the steps of:

a. receiving, via an interface unit, a request to initiate the determination of operating and/or dimensioning parameters of the gas treatment plant, wherein the request comprises gas treatment unit input parameters for the one or more gas treatment unit(s), wherein the gas treatment unit input parameters include at least one relative parameter which is independent of the plant throughput, b. initializing, via a determination processing unit, a digital model of the gas treatment plant based on the gas treatment unit input parameters and including a relation of the at least one relative parameter to a corresponding parameter, wherein the corresponding parameter is dependent on the plant throughput or dependent on the gas treatment unit geometry and is a result of the relation to the at least one relative parameter, wherein the digital model characterizes a mass and heat transfer in the gas treatment plant including the one or more gas treatment unit(s), c. determining, via the determination processing unit, operating and/or dimensioning parameters of the gas treatment plant including the corresponding parameter based on the digital model, d. outputting, via an output interface, the operating and/or dimensioning parameters including the corresponding parameter dependent on the plant throughput or dependent on the gas treatment unit geometry, which is particularly a result of the relation to the at least one relative parameter provided as gas treatment unit input parameter.

The present invention further relates to a method, particularly a computer-implemented method, for determining operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment unit(s), wherein one of the one or more gas treatment unit(s) is an absorber, wherein the method may be carried out by a computer or a distributed computer system, the method comprising the steps of:

a. receiving, via an interface unit, a request to initiate the determination of operating and/or dimensioning parameters of the gas treatment plant, wherein the request comprises absorber input parameters, wherein the absorber input parameters include a loading factor indicating a distance to an equilibrium capture capacity of the treatment solution in the absorber, b. initializing, via a determination processing unit, a digital model of the gas treatment plant based on the absorber input parameters and including a relation of the loading factor to a flow rate, wherein the digital model characterizes a mass and heat transfer in the gas treatment plant including the absorber, c. determining, via the determination processing unit, operating and/or dimensioning parameters of the gas treatment plant including the flow rate based on the digital model, d. outputting, via an output interface, the operating and/or dimensioning parameters including the flow rate, which is a result of the relation to the loading factor provided as gas treatment unit input parameter.

The present invention further relates to a computer program or computer program product with computer-readable instructions that, when executed on one or more processor(s), cause the processor(s) to perform methods for determining operating and/or dimensioning parameters of a gas treatment plant for treating as described herein. The present invention further relates to a computer readable non-volatile or non-transitory storage medium with computer-readable instructions that, when executed on one or more a processor(s), cause the processor(s) to perform methods for determining operating and/or dimensioning parameters of a gas treatment plant for treating as described herein.

The present invention further relates to a system for determining operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, the system comprising:

a. an interface unit, which is configured to receive a request to initiate the determination of operating and/or dimensioning parameters of the gas treatment plant, wherein the request comprises gas treatment unit input parameters for the one or more gas treatment unit(s), wherein the gas treatment unit input parameters include at least one relative parameter which is independent of the plant throughput, b. a determination processing unit, which is configured to initialize a digital model of the gas treatment plant based on the gas treatment unit input parameters and including a relation of the at least one relative parameter to a corresponding parameter, wherein the corresponding parameter is dependent on the plant throughput or dependent on a gas treatment unit geometry and is a result of a relation to the at least one relative parameter, wherein the digital model characterizes a mass and heat transfer in the gas treatment plant including the one or more gas treatment unit(s), and which is configured to determine operating and/or dimensioning parameters of the gas treatment plant including the corresponding parameter based on the digital model, and c. an output interface, which is configured to output the operating and/or dimensioning parameters including the corresponding parameter dependent on the plant throughput or dependent on the gas treatment unit geometry, which is particularly a result of the relation to the at least one relative parameter provided as gas treatment unit input parameter.

The present invention further relates to a system for determining operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein one gas treatment unit is an absorber for treating a gaseous inlet stream with a treatment solution to provide a treated outlet stream, the system comprising:

a. an interface unit, which is configured to receive a request to initiate the determination of operating and/or dimensioning parameters of the gas treatment plant, wherein the request comprises absorber input parameters, wherein the absorber input parameters include a loading factor indicating the distance to an equilibrium capture capacity of the treatment solution in the absorber, b. a determination processing unit, which is configured to initialize a digital model of the gas treatment plant based on the absorber input parameters and including a relation of the loading factor to a flow rate, wherein the digital model characterizes a mass and heat transfer in the gas treatment plant including the absorber, and which is configured to determine operating and/or dimensioning parameters of the gas treatment plant including the flow rate based on the digital model, c. an output interface, which is configured to output the operating and/or dimensioning parameters including the flow rate, which is particularly a result of the relation to the loading factor provided as gas treatment unit input parameter.

The present invention further relates to a method for constructing or building a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, wherein the method may be carried out by a computer or a distributed computer system, the method including the steps of:
  a. determining a design for the gas treatment plant including the determination of operating and/or dimensioning parameters of the gas treatment plant according to one or more method(s) set out herein,
  b. constructing or building the gas treatment plant according to or based on the determined design.

The present invention further relates to a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, which is built according to or based on a design for the gas treatment plant, wherein the design includes the determination of operating and/or dimensioning parameters of the gas treatment plant according to one or more method(s) set out herein.

The present invention further relates to a method, particularly a computer-implemented method, for generating a request to initiate the determination of operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the method may be carried out by a computer or a distributed computer system, wherein the generation includes providing gas treatment unit input parameters according to a permission object, wherein the permission object defines which gas treatment unit input parameters are provided as relative parameter, wherein such relative parameter is independent of the plant throughput and relates to at least one corresponding parameter that depends on the plant throughput or depends on the gas treatment unit geometry.

The present invention further relates to a client device comprising an input unit for generating a request to initiate the determination of operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the input unit is configured to provide gas treatment unit input parameters according to a permission object, wherein the permission object defines which gas treatment unit input parameters are provided as relative parameter, wherein such relative parameter is independent of the plant throughput and relates to at least one corresponding parameter that depends on the plant throughput or dependent on the gas treatment unit geometry.

The present invention further relates to a method, particularly a computer-implemented method, for generating a request to initiate the determination of operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the method may be carried out by a computer or a distributed computer system, wherein the generation includes providing process specific input parameters according to a permission object, wherein the permission object defines which process specific input parameters are provided based on an industry application type.

The present invention further relates to a client device comprising an input unit or an input unit for generating a request to initiate the determination of operating and/or dimensioning parameters of a gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the input unit is configured to provide process specific input parameters according to a permission object, wherein the permission object defines which process specific input parameters are provided based on an industry application type.

The present invention further relates to a method, particularly a computer-implemented method, for generating a request to initiate the determination of operating parameters to operate an existing gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the method may be carried out by a computer or a distributed computer system, wherein the generation includes providing process specific input parameters according to a permission object, wherein the permission object defines which process specific input parameters are provided based on an industry application type or wherein the generation includes providing gas treatment unit input parameters or according to a permission object, wherein the permission object defines, if a flow rate in a gas treatment unit or a composition specifying a proportion of one or more depleted component(s) in the treated outlet stream is provided as gas treatment unit input parameter.

The present invention further relates to a client device comprising an input unit or an input unit for generating a request to initiate the determination of operating parameters to operate an existing gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the input unit is configured to provide process specific input parameters according to a permission object, wherein the permission object defines which process specific input parameters are provided based on an industry application type or wherein the input unit is configured to provide gas treatment unit input parameters according to a permission object, wherein the permission object defines, if a flow rate in a gas treatment unit or a composition specifying a proportion of one or more depleted component(s) in the treated outlet stream is provided as gas treatment unit input parameter.

The present invention further relates to a method, particularly a computer-implemented method, for determining operating parameters to operate an existing gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, wherein the method may be carried out by a computer or a distributed computer system, the method comprising the steps:
   a. generating a request to initiate the determination of operating parameters to operate an existing gas treatment plant, wherein the generation includes providing process specific input parameters according to a permission object, wherein the permission object defines which process specific input parameters are provided based on an industry application type or wherein the generation includes providing gas treatment unit input parameters according to a permission object, wherein the permission object defines, if a flow rate in a gas treatment unit or a composition specifying a proportion of one or more depleted component(s) in the treated outlet stream is provided as gas treatment unit input parameter,
   b. initializing, via a determination processing unit, a digital model of the gas treatment plant based on the process specific parameters or the gas treatment unit input parameters provided in the generated request, wherein the digital model characterizes a mass and heat transfer in the gas treatment plant,
   c. determining, via the determination processing unit, operating parameters of the existing gas treatment plant based on the digital model,
   d. outputting, via an output interface, the determined operating parameters including particularly the flow rate in the gas treatment unit or the composition specifying a proportion of one or more depleted component(s) in the treated outlet stream.

The present invention further relates to a system for determining operating parameters to operate an existing gas treatment plant for treating a gaseous inlet stream with a treatment solution to provide a treated outlet stream, preferably an acid gas removal plant for removing one or more acid gas component(s) from a gaseous inlet stream with a treatment solution to provide a treated outlet stream, including one or more gas treatment units, the system comprising:
   a. an input unit configured to generate a request to initiate the determination of operating parameters to operate an existing gas treatment plant, wherein the generation includes providing process specific input parameters according to a permission object, wherein the permission object defines which process specific input parameters are provided based on an industry application type or wherein the generation includes providing gas treatment unit input parameters according to a permission object, wherein the permission object defines, if a flow rate in a gas treatment unit or a composition specifying a proportion of one or more depleted component(s) in the treated outlet stream is provided as gas treatment unit input parameter,
   b. a determination processing unit configured to initialize a digital model of the gas treatment plant based on the process specific parameters or the gas treatment unit input parameters provided in the generated request, wherein the digital model characterizes a mass and heat transfer in the gas treatment plant, and configured to determine operating parameters of the existing gas treatment plant based on the digital model,
   c. an output interface configured to output the determined operating parameters including particularly the flow rate in the gas treatment unit or the composition specifying a proportion of one or more depleted component(s) in the treated outlet stream.

The present invention further relates to a computer program or computer program product with computer-readable instructions that, when executed on one or more processor(s), cause the processor(s) to perform methods for generating a request to initiate the determination of operating and/or dimensioning parameters or methods for generating a request to initiate the determination of operating parameters to operate an existing gas treatment plant as described herein. The present invention further relates to a computer readable non-volatile or non-transitory storage medium with computer-readable instructions that, when executed on one or more a processor(s), cause the processor(s) to perform methods for generating a request to initiate the determination of operating and/or dimensioning parameters or methods for generating a request to initiate the determination of operating parameters to operate an existing gas treatment plant as described herein.

The present invention advantageously enables an optimized design process and subsequently generated design of gas treatment plants, preferably acid gas removal plants based on modelled and determined parameters.

For example, relative parameters are introduced, which enables a simpler design process, since the relative parameters are problem or functionally driven, whereas corresponding parameters require the user to translate the problem or functionally driven specification of the gas treatment plant into a specific structural, dimensional or operational parameters. Moreover, the design constraints are easier to foresee in terms of the relative, e.g. functionally driven, parameters than in terms of any structural, dimensional or operational parameters. As such the ability to produce physically meaningful results is greatly enhanced. In particular no expert knowledge is required to perform determinations of the operating and/or dimensioning parameters for gas treatment plants, since no expert knowledge is required to specify.

The present invention enables the design of gas treatment plants, preferably acid gas removal plants, based on functionally driven or relative parameters rather than structurally, dimensionally, operationally driven or corresponding parameters. Since the relative parameters are introduced, respective corresponding parameters are determined as an output of the method. Additionally, by introducing relative parameters any correlations of input parameters are reduced or led back allowing for more robust and stable determination of the dimensioning and/or operating parameters, which are implemented in a gas treatment plant to be physically built. Thus the complexity of the design process is reduced in view of the number of iterations required to find physically and chemically meaningful operating and/or dimensioning parameters. Hence the computer program, when loaded into a processing system and executed, transforms the system overall from a general-purpose computing system into a special-purpose computing system customized to an environment for simplified and more efficient gas treatment plant design.

Additionally, the permission object set on the input unit level for generating the request enables enhanced control over the design as well as the rating process in view of the input parameters required for such simplified and more efficient gas treatment plant design or rating. Here design refers to determinations with respect to gas treatment plants to be built or implemented and rating refers to determinations with respect to existing or physically built gas treatment plants. In design cases operating and/or dimensioning parameters may be determined, that signify the operating parameters and dimensioning parameters of a gas treatment plant to be built. Such operating parameters are e.g. the flow rate in the absorber, the composition of outlet streams, internal streams or inlet streams for the one or more gas treatment units. Dimensioning parameters are e.g. diameter or height of the one or more gas treatment units. In rating cases operating parameters may be determined, that signify the operating conditions in an existing plant. Such operating parameters are e.g. composition of outlet streams, internal streams or inlet streams for the one or more gas treatment units, any temperatures, mass or volume flows. Operating parameters may be determined, which are used to operate the existing gas treatment plant and which can be adjusted in operation of the physically built gas treatment plant. The permission object set on the input level further reduces the solution space in such a way that physically and chemically meaningful operating and/or dimensioning parameters are determined, which when implemented in the physically built gas treatment plant lead to stable operation of the gas treatment plant. Moreover, any scenarios resulting in physically and chemically not meaningful operating and/or dimensioning parameters can be avoided and the number of iterations to reach a meaningful solution is reduced, thus using computer resources in a very efficient way.

Certain embodiments of the present invention further advantageously provide a graphical user interface that utilizes a grouped hierarchical structure for input parameters, thus improving upon the usability of the graphical user interface by allowing the user to more efficiently specify the input parameters.

The following description relates to the methods, the computer programs, the computer readable storage media, the input units, the systems, the method for constructing or building a gas treatment plant as well as the gas treatment plant lined out above. In particular the systems, the input units, the computer programs and the computer readable storage media are configured to perform the method steps as set out above and further described below.

A computer program may be stored and/or distributed on a suitable medium, such as an optical storage medium or a solid-state medium supplied together with or as part of other hard-ware, but may also be distributed in other forms, such as via the internet or other wired or wireless telecommunication systems.

However, the computer program may also be presented over a network like the World Wide Web and can be downloaded into the working memory of a data processor from such a network.

According to a further exemplary embodiment of the present invention, a data carrier or a data storage medium for making a computer program element available for downloading is provided, which computer program element is arranged to perform a method according to one of the previously described embodiments of the present invention.

The term "input parameter" as defined by the present invention may be understood as any parameter to be provided by a user or provided via a database and required to initialize a digital model for simulating or designing a gas treatment plant.

The term "relative parameter" as used herein relates to a corresponding parameter. If the relative parameter is provided in the gas treatment unit input parameters the corresponding parameter will not be specified, but will be a result of the determination. Hence this is an exclusive specification of either the relative parameter or the corresponding parameter provided in the gas treatment unit input parameters. The relative parameter is as such independent of the plant throughput and not directly correlated or not directly related to the plant throughput. In contrast the corresponding parameter as such depends on the plant throughput or depends on the gas treatment unit geometry and is directly correlated or directly related to the plant throughput or the gas treatment unit geometry. Here the term "throughput" refers to a mass throughput or a volume throughput and the term "gas treatment unit geometry" refers to a structural arrangement of the gas treatment unit which as such depends on or is directly correlated or directly related to the physical dimensions, such as a height or a diameter of the gas treatment unit. In a particular example, the relative parameter may be independent of or not correlated to a plant scale and/or a capacity of the gas treatment plant. Relative parameters may be functional parameters, which in contrast to the corresponding parameters are not directly correlated to the plant throughput, the plant scale and/or the capacity of the gas treatment plant. One example for a relative parameter of the absorber is the hydraulic load in the absorber. This parameter is a functional parameter in specifying a criterium as distance to hydraulic flooding rather than the absorber diameter. In contrast the corresponding parameter, in this example, the absorber diameter signifies a physical dimension of the absorber and directly depends on the plant throughput, the plant scale, and/or the capacity of the gas treatment plant. Whereas the specification of an unsuitable absorber diameter could lead to flooding conditions and unstable or physically not meaningful operating conditions, the specification of a hydraulic load, e.g. via a safety factor less than 1 and greater than 0.5, inherently avoids design of unstable or unreasonable conditions.

In one embodiment wherein one of the one or more gas treatment units is an absorber, particularly for treating a gaseous inlet stream with a treatment solution to provide a treated outlet stream, wherein absorber input parameters are provided including at least one of the following relative parameters:
 i. a composition specifying a proportion of one or more depleted component(s) in the treated outlet stream,
 ii. a loading factor indicating a distance to an equilibrium capture capacity of the treatment solution in the absorber,
 iii. an acceptable hydraulic load indicative of a flooding condition in the absorber.

In one example the absorber input parameters include all available relative parameters out of i, ii and iii and no corresponding parameter, since such corresponding parameters are a result of the determination based on such absorber input parameters. In another example the absorber input parameters include two of the available relative parameters and the remaining absorber input parameters are specified via the corresponding parameters. In yet another example the absorber input parameters include one of the available relative parameters and the remaining absorber input parameters are specified via the corresponding parameters.

In one example the absorber input parameters only indirectly include at least one of the absorber height, the absorber diameter or the solution flow rate in terms of a relative parameter by providing:
 for the absorber height, a composition in the treated outlet stream,
 for the flow rate, a loading factor of the treatment solution in the absorber,
 for the absorber diameter, an acceptable hydraulic load for the absorber.

Following this rational, the absorber height, the flow rate and the absorber diameter are corresponding parameters respectively and as such part of the operating and/or dimensioning parameters, which will be determined based on the digital model. In particular the absorber diameter and height are dimensioning parameters and the flow rate is an operating parameter.

Based on the above parameters the concept of providing relative parameters is more apparent. For instance, the composition in the treated outlet stream is relative and in this specific case may be dimensionless in the sense that it may be determined by the ratio of the amount of one or more component(s) to be absorbed residing in the treated outlet stream to the sum of the amount of all components in the treated outlet stream. This ratio relates to the absorber height, since the amount of one or more component(s) to be absorbed changes as the path through the absorber increases. Similarly, the loading factor is relative and in this specific case may be dimensionless in the sense that it may be determined by the ratio of actual loading to equilibrium loading. This ratio relates to the treatment solution flow rate, since the actual loading decreases as the treatment solution flow rate or flow rate increases. The hydraulic load is relative and in this specific case may be dimensionless in the sense that it may be determined by the ratio of the actual hydraulic load to the hydraulic load at flooding limit. This ratio relates to the absorber diameter, since the actual hydraulic load decreases as the diameter of the absorber increases. Hence relative parameters in the sense of the present invention relate to functionally driven parameters, which are preferably based on ratios, fractions or similar relations resulting in parameters, which are related or correlated to corresponding parameters. Such relative parameters may carry a dimension such as the loading factor with a dimension $m^3/h/m^2$ or the F-factor with $m/s*Pa^0.5$. In alternative embodiments the relative parameter may be dimensionless referring to any quantity, to which no physical dimension in terms of a unit is assigned or to which a relative unit in terms of percentage or the like is assigned. Such relative parameters are independent or not directly correlated to the plant throughput, the plant scale, the physical dimensions of the plant and/or the capacity of the gas treatment plant.

In providing relative parameters for the absorber, no specification of the absorber height, the absorber diameter or the flow rate is required. Instead the composition in the treated outlet stream, the acceptable hydraulic load or the loading factor of the treatment solution in the absorber are provided. The composition in the treated outlet stream may be determined by the ratio of the amount of one or more component(s) to be absorbed residing in the treated outlet stream to the sum of the amount of all components in the treated outlet stream.

The composition specifying a proportion of one or more depleted gas component(s) in the treated outlet stream may be based on individual proportion(s) for each depleted gas component(s) in the treated outlet stream. The composition may also be based on a sum or partial sum of proportions of depleted gas components in the treated outlet stream.

The loading factor indicating the distance to the equilibrium capture capacity of the treatment solution may be determined based on the equilibrium loading and actual loading. For the actual or equilibrium loading the gas phase or gaseous stream in the absorber and the liquid phase or treatment solution in the absorber may be considered or determined at the same height of the absorber.

Here the equilibrium loading refers to the maximum amount of one or more gas component(s) absorbed in the treatment solution under conditions of Vapor Liquid Equilibrium (VLE). Hence the equilibrium loading signifies a point, where no mass or gas component transfer from the gas phase or the gaseous stream into the treatment solution occurs in the absorber. In other words, in equilibrium the treatment solution is saturated with respect to one or more gas components. The equilibrium loading of any gas component in the treatment solution may be based on an absorption medium composition, a treatment solution temperature, a pressure and a composition of the gas phase or the gaseous stream in the absorber, wherein the VLE is determined based on gas and liquid phase at the same absorber height. Here absorption medium refers to the liquid phase free of any absorbed components from the gas phase or gaseous stream and the treatment solution refers to the liquid phase including any absorbed components from the gas phase or gaseous stream.

The actual loading refers to the amount of one or more gas component(s) actually present in the treatment solution. The actual loading of one or more gas component(s) in the treatment solution may be based on an actual gas component flow rate in the treatment solution and an actual total flow rate of the treatment solution or an actual total flow rate of the absorption medium. In particular the actual loading of any gas component in the treatment solution may be based on the ratio of the actual gas component flow rate in the treatment solution to the actual total flow rate of the treatment solution or the actual total flow rate of the absorption medium.

The loading factor of the treatment solution may be determined by an extremum of the ratio of actual loading to equilibrium loading or vice versa by the ratio of equilibrium loading to actual loading along the absorber height. Here the extremum may be a maximum or minimum. Alternatively or additionally the loading factor of the treatment solution may be determined by the ratio of actual loading to equilibrium loading or vice versa by the ratio of equilibrium loading to actual loading at the absorber bottom. In case of the ratio of actual loading to equilibrium loading the loading factor may be defined such that a loading factor of 1 signifies the equilibrium loading with no mass transfer occurring. For loading factors less than 1 absorption takes place and for loading factors greater than 1 desorption takes place. In case of the ratio of equilibrium loading to actual loading the loading factor may be defined such that a loading factor of 1 signifies the equilibrium loading with no mass transfer occurring. For loading factors greater than 1 absorption takes place and for loading factors less than 1 desorption takes place.

The loading factor of a gas component i may be defined as follows:

The loading factor of any gas component i may be related to the ratio of an actual gas loading of component i, which is a function of an actual gas component flow rate of component i in liquid solution and an actual total flow rate of liquid solution, to the equilibrium gas loading of any gas component i, which is a function of a absorption medium composition, temperature, pressure and composition of gas phase.

The acceptable hydraulic load indicates an acceptable hydraulic operational regime in the absorber. It may be determined by a distance of the actual hydraulic load to hydraulic flooding conditions. Here, hydraulic flooding conditions refer to operating conditions, where a further increase in gas or liquid flow in the absorber will lead to flooding of the absorber internals, or liquid is completely entrained by the gas flow. The hydraulic load can be specified via the ratio of the actual hydraulic load in the absorber to the hydraulic load at flooding limit. The acceptable hydraulic load may be related to or indicative of a flooding condition in the absorber, e.g. a flooding curve or a column mass transfer height specific pressure drop in the absorber.

The acceptable hydraulic load may be defined as follows:
The hydraulic load may be related to the ratio of an actual hydraulic load, which is a function of an F-Factor and a liquid velocity wL, to an hydraulic load at flooding limit, which is a function of the F-Factor, the liquid velocity wL, a gas density of the gaseous stream in the absorber, a liquid density of the treatment solution, a gas viscosity density of the gaseous stream in the absorber, a liquid viscosity of the treatment solution, a liquid surface tension of the treatment solution and a geometry of the mass transfer or absorber internals. In this context the hydraulic load may be determined for a constant liquid to gas ratio, for constant F-Factor or for constant liquid verlocity wL. Here the F-Factor may be defined as $F\text{-Factor}=\text{gas velocity}*(\text{gas density})^{\wedge}0,5.$ Additionally or alternatively the hydraulic load in the absorber may be based on the F-Factor or the liquid velocity as relative parameter. In such case the operating and/or dimensioning parameters and specifically the absorber diameter is determined based on the given F-Factor or liquid velocity. Once such determination is performed a further check may be performed by determining, if the resulting absorber diameter allows for an acceptable hydraulic operational regime in the absorber, such that flooding conditions are avoided. If the determined absorber diameter does not allow for an acceptable hydraulic operational regime in the absorber, such that flooding conditions are met, the determination of operating and/or dimensioning parameters will be resumed or a warning will be provided via the output interface. Such warning may further be provided to the input unit, where it may be displayed to a user.

The expression hydraulic load may also be alluded to as capacity in %, safety factor, or loading point.

Particularly, in providing the composition in the treated outlet stream, the acceptable hydraulic load or the loading factor of the treatment solution make the specification of the absorber height, absorber diameter or the flow rate redundant. Thus, absorber height, absorber diameter or flow rate are released parameters in the digital model and are as such a result of the method in the form of dimensioning and/or operating parameters. This enables the input parameters to be specified in a single step such that the result is generated without requiring further manual interactions by the designer. A more robust convergence with less iterations and hence more efficiency in the design process and in the use of computing power is a result. Lastly, the use of the method is less error-prone, simpler and leads to a more effective process in determining the chemically and physically meaningful dimensioning and/or operating conditions of the gas treatment plant.

In a further embodiment the absorber input parameters include the loading factor of the treatment solution, which is determined by the ratio of actual loading, preferred actual gas loading, to equilibrium loading, preferred equilibrium gas loading, at the absorber bottom. Alternatively, the absorber input parameters include the loading factor of the treatment solution, which is determined by an extremum, e.g. a maximum or minimum, of the ratio of actual loading, preferred actual gas loading, to equilibrium loading, preferred equilibrium gas loading, along the absorber height. In this embodiment the extremum may be determined via the profile of the loading factor along the absorber height, wherein the extremum signifies a point of the profile where the first derivative is zero and the second derivative is greater or smaller than zero. The profile may be defined such that the extremum is a maximum.

In a further embodiment the loading factor determined by the ratio of actual loading to equilibrium loading of the treatment solution is less than 1, preferably ≤0.95 and particularly preferred ≤0.9. Here the values may be viewed in terms of a modulus. In such embodiments the full absorber height or a part of the absorber height may be taken into account. For example, the part of the absorber height from the bottom of the absorber to a fraction to the top of the absorber height such as a fraction of 0.9 or 0.8 or a fraction of 0.7 to 0.9 to the top may be taken into account. Using the loading factor in such a way avoids unreasonable or physically not meaningful specifications for determining the dimensioning and/or operating parameters, since there is often no or a very minor mass transfer at the top of the absorber and, hence, only the thermodynamically important part of the absorber is taken into account.

In a further embodiment the loading factor of the treatment solution is determined based on at least one gas component to be absorbed from the inlet stream. In a further embodiment, where more than one gas component to be absorbed is present in the inlet stream, the loading factor is determined as combined loading factor including the more than one gas components to be absorbed from the inlet stream. The combined loading factor accounts for interdependencies between the gas components to be absorbed. Such a combined loading factor reflects thermodynamic as well as kinetic properties of the treatment solution in connection with the gas components to be absorbed. Thus, reasonable or physically meaningful results in determining the dimensioning and/or operating parameters can be ensured.

The combined loading factor may be related to the ratio of an actual loading, which depends on actual gas component flow rates for at least two or more gas components in the treatment solution and an actual total flow rate of the treatment solution or the actual total flow rate of the absorption medium, to equilibrium loading, which depends on absorption medium composition, treatment solution temperature, pressure and composition of the gas phase or the gaseous inlet stream, wherein the VLE is determined based on gas and liquid phase at the same absorber height. Here absorption medium is the liquid phase free of any absorbed components from the gas phase and solution is the liquid phase including any absorbed components.

In a further embodiment the absorber input parameters include configuration parameters specifying the absorber configuration. Such configuration parameters may further specify a column type such as packed bed or tray column, a number of segments in the column, pressure conditions like the pressure drop over the column, temperature conditions or a distributor type for the liquid treatment solution.

In a further embodiment process specific input parameters are provided, which are comprised in the request and are used to initialize the digital model. The process specific input parameters may include absorber input parameters, regenerator input parameters as well as the composition of the gaseous inlet stream at the absorber inlet and absorption medium parameters specifying properties of the treatment solution. If apart from the absorber further gas treatment units or process units are present, the process specific input parameters preferably include further parameters specifying each of the gas treatment units. Alternatively, some of the parameters specifying further gas treatment units may be pre-set to simplify and reduce the number of process specific input parameters.

The gas treatment plant may include one or more gas treatment units such as one or more absorber(s), one or more regenerator(s) and/or further gas treatment units. Additionally process units such as heat exchangers, pumps, gas compressors or a gas condensers may be included in the gas treatment plant and reflected in the digital model via respective unit operations. The gas treatment plant may include one or more of these gas treatment units or process units. Preferably, the process specific input parameters include configuration parameters, which specify the gas treatment and/or process units included in the gas treatment plant and their interconnection representing streams. Further, the configuration parameters may be fully or partly pre-defined providing a fixed set of possible configurations. Such pre-defined configurations may be stored in a database and can be identified in the process specific input parameters via one or more identifier(s) signifying the respective configuration parameters. Pre-defined configuration parameters guide the user by reducing the problem space and lead to a more robust and stable determination of operating and/or dimensioning parameters. In embodiments where the configurations are not fully predefined the method can include a validation step to ensure sensible configurations are defined by the user.

In a further embodiment the gas treatment unit includes a regenerator preferably with at least one reboiler for regenerating the treatment solution and feeding the regenerated treatment solution back into the absorber, wherein regenerator input parameters are provided including at least one of the following relative parameters:

a fraction quality of the regenerated treatment solution or lean solution, a strip steam ratio, or a loading factor indicating a distance to an equilibrium capture capacity of the regenerated treatment solution or lean solution at an absorber top;

an acceptable hydraulic load indicating an acceptable hydraulic operational regime in the regenerator.

The regenerator input parameters may include only indirectly at least one of the reboiler duty or the regenerator diameter in terms of relative parameters by providing:

for the reboiler duty, the fraction quality of the regenerated treatment solution or strip steam ratio or a loading factor of one component at the absorber top, for the regenerator diameter, an acceptable hydraulic load for the regenerator.

In one example the regenerator input parameters include all available relative parameters. In another example the regenerator input parameters include one of the available relative parameters and the remaining regenerator input parameters are specified via the corresponding parameters.

Here the reboiler duty refers to the heat duty requirement of the regenerator, which has a significant impact on the energy consumption of the gas treatment plant. The regenerator input parameters may not include at least one of the reboiler duty or the regenerator diameter. Instead the fraction quality of the regenerated treatment solution or lean solution, the strip steam ratio, or the loading factor of the regenerated treatment solution or lean solution at the absorber top or the acceptable hydraulic load may be provided.

The fraction quality of the regenerated treatment solution or lean solution refers to the concentration of one or more gas components that remain in the lean solution after regeneration. The fraction quality may be viewed as a composition specifying a proportion of one or more remaining gas component(s) in the lean solution.

The strip steam ratio may be based on a water flow rate in regeneration and an acid gas flow rate in regeneration. The strip steam ratio may be defined by the ratio of the water vapor or gas phase flow rate in regeneration to the acid gas vapor or gas phase flow rate in regeneration. This may be determined for constant height, e.g. at the top or between bottom and top.

The acceptable hydraulic load indicates an acceptable hydraulic operational regime in the regenerator. It may be determined by a distance of the actual hydraulic load to hydraulic flooding conditions. Here, hydraulic flooding conditions refer to operating conditions, where a further increase in gas or liquid flow in the regenerator will lead to flooding of the regenerator internals, or liquid is completely entrained by the gas flow. The hydraulic load can be specified via the ratio of the actual hydraulic load in the regenerator in operation to the hydraulic load at flooding limit. The acceptable hydraulic load may be related to or indicative of a flooding condition in the regenerator, e.g. a flooding curve or a column mass transfer height specific pressure drop in the regenerator.

The acceptable hydraulic load may be defined as follows:

The hydraulic load may be related to the ratio of an actual hydraulic load, which is a function of an F-Factor and a liquid velocity wL, to an hydraulic load at flooding limit, which is a function of the F-Factor, the liquid velocity wL, a gas density of the gaseous inlet stream, a liquid density of the treatment solution, a gas viscosity density of the gaseous inlet stream, a liquid viscosity of the treatment solution and a liquid surface tension of the treatment solution and a geometry of the mass transfer or absorber internals. In this context the hydraulic load may be determined for a constant liquid to gas ratio, for constant F-Factor or for constant liquid verlocity wL. Here the F-Factor may be defined as $$F\text{-Factor}=\text{gas velocity}*(\text{gas density})^{\hat{}}0,5.$$

Additionally or alternatively the hydraulic load in the regenerator may be based on the F-Factor or the liquid velocity as relative parameter. In such case the operating and/or dimensioning parameters and specifically the regenerator diameter is determined based on the given F-Factor or liquid velocity. Once such determination is performed a further check may be performed by determining, if with the resulting regenerator diameter allows for an acceptable hydraulic operational regime in the regenerator, such that flooding conditions are avoided. If the determined regenerator diameter does not allow for an acceptable hydraulic operational regime in the regenerator, such that flooding conditions are met, the determination of operating and/or dimensioning parameters will be resumed or a warning will be provided via the output interface. Such warning may further be provided to the input unit, where it may be displayed to a user.

The expression hydraulic load may also be alluded to as capacity in %, safety factor, or loading point.

Loading factor at the absorber top may be determined as discussed above for the absorber. Here the loading factor at the absorber top may be used as regenerator input parameter to ensure sufficient driving force at the absorber top. The corresponding parameter is the reboiler duty.

In a further embodiment the regenerator input parameters include configuration parameters specifying the regenerator configuration. Such configuration parameters may further specify a regenerator column type such as the regenerator internals like packed bed or tray column, a number of segments in the column, pressure conditions like the absolute pressure, or the pressure drop over the column or temperature conditions.

In a further embodiment the methods for determining dimensioning and/or operating parameters include a further step after receipt of the request and prior to initializing the digital model of the gas treatment plant. The further step may include to provide thermodynamic parameters via a database unit, wherein the thermodynamic parameters are derived from measurements of thermodynamic properties of gas treatment plants under operating conditions. The thermodynamic parameters are preferably indicative of thermodynamic properties in gas treatment plants under operating conditions. If such thermodynamic parameters are provided the initialization of the digital model of the gas treatment plant is based on the process specific input parameters including any gas treatment unit parameters and the thermodynamic parameters.

In a further embodiment providing thermodynamic parameters indicative of thermodynamic properties in gas treatment plants under operating conditions may include data that is stored in a database unit. Such data complements the input parameters and thus reduces the number of parameters that must be provided by a user. Preferably the thermodynamic parameters are based on historical measurement data of operating gas treatment plants or lab scale experiments to provide a more accurate basis for the determination of the operating and/or dimensioning parameters. The thermodynamic parameters may comprise thermodynamic absorption medium-gas parameters specifying equilibrium conditions, kinetic parameters such as reaction rate or mass transfer parameters relating to density, viscosity, surface tension, diffusion coefficients or mass transfer correlations. Specifically including kinetic parameters enhances accuracy of the determined operating and/or dimensioning parameters, since not only the equilibrium conditions are accounted for.

In a preferred embodiment the at least one relative parameter comprised in the request lies within a pre-defined range. Here one or more of the above absorber input parameters or regenerator input parameters specified as relative parameters may lie within a pre-defined range. In a further embodiment a validation step is performed for the at least one relative parameter before and/or after receipt of the request, wherein the at least one relative parameter is valid, if it lies within a pre-defined range. Such validation step may be implemented via a permission object before receipt of the request e.g. on input unit level and/or as separate validation step after receipt of the request e.g. on determination unit level. In particular, the initialization of the digital model may be performed, if the relative parameter is determined to be valid. If the relative parameter is determined not to be valid, a warning is provided via the output interface and optionally displayed via the input unit to a user.

In a further embodiment the physical performance of the gas treatment plant is described by the process specific input parameters including the gas treatment unit input parameters and thermodynamic parameters, and the operating and/or dimensioning parameters in connection with the digital model. Here the digital model may include a system of equations defining unit operations in the form of the one or more gas treatment unit(s) or process unit(s) of the gas treatment plant. The digital model may include any gas treatment unit or process unit specified via the configuration parameters. For instance, the digital model may include an absorber and/or a regenerator model characterizing the mass and heat transfer in the absorber and/or regenerator, respectively. The digital model is hence a vehicle to reliably and accurately describe the gas treatment plant and such description is used to make reliable and accurate predictions on the dimensioning and/or operating parameters to be implemented in the physical gas treatment plant to be built. The digital model may be based on MESH equations (Material balances, Equilibrium relations, Summation equations, Heat balances) or may be based on MERSHQ equations (Material balances, Energy balances, mass and heat-transfer Rate equations, Summation equations, Hydraulic equations for pressure drop, eQuilibrium equations) and optionally cost equations for e.g. operational and/or capital expenditures may be included, as known in the art [Ralf Goedecke; Fluidverfahrenstechnik, Grundlagen, Methodik, Technik, Praxis; 2011; WILEY-VCH Verlag GmbH & Co., Weinheim, Germany; ISBN: 978-3-527-33270-01.

In a further embodiment determining dimensioning and/or operating parameters includes using an equation-based solution method or a sequential-modular solution method for the digital model. In sequential-modular solution methods unit operations are solved in sequence, starting with the gaseous inlet stream and sequentially solving downstream unit operations such as the absorber unit operation or the regenerator unit operation. Here each unit operation of the gas treatment plant is represented by a system of equations. The multiple systems of equations are solved sequentially for each unit operation. To reach a result feedback loops are integrated, which match one or more output(s) of one of the unit operations to the corresponding one or more input(s) of another connected unit operation. One example is the result for the composition of the lean solution in the output stream of the regenerator as determined from the system of equations for the regenerator unit operation and the result for the composition of the lean solution in the inlet stream of the absorber as determined from the system of equations for the absorber unit operation. Such built in directionality from inlets to outlets make downstream specifications, e.g. composition of the outlet stream, difficult. This can be overcome by introducing control loops, which control the downstream specifications, e.g. composition of the outlet stream, strip steam ratio, hydraulic load or loading factor. Such a control loop may be based on relative parameter(s) as control parameter(s). It may determine stepwise the difference to a control parameter, such as the composition of the outlet stream, which adds to the complexity, increases calculation time and slows down the processor. Alternatively, by providing relative parameter(s) the unit operations can be modified in such a way to include the relation to the corresponding parameter(s) in the respective unit operation and to determine the corresponding parameter as result of the determination of operating and/or dimensioning parameters.

In equation-based solution methods the unit operations are treated as a set of equations to be solved simultaneously. Here all unit operations and potentially feedback loops of the gas treatment plant are represented in a single system of equations for the gas treatment plant. The system of equations is solved simultaneously for all unit operations and potentially feedback loops. The system of equations may be solved numerically by simultaneously fulfilling all equations with a defined accuracy. Finding the solution for the system of equations may include more than one iteration. The use of an equation-based solution method enables a simple specification of relative parameters, which is simpler than in sequential-modular solution methods. Moreover, in an equation-based solution method it is important to specify meaningful starting or initial input parameters such that the method finds an appropriate starting profile to get to a solution. The specification of relative parameters for the gas treatment unit input parameters provides a simple way to provide meaningful starting or initial input parameters and to select starting profiles.

Providing at least one of the above relative parameters in the gas treatment unit input parameters may affect the digital model in that the digital model includes the relation to the corresponding parameter. For the absorber input parameters this may include one or more relations of at least one of the composition in the treated outlet stream to the absorber height, the loading factor of the treatment solution in the absorber to the flow rate or the acceptable hydraulic load to the absorber diameter, respectively. Similarly, the relations for the regenerator input parameters may be included. Determining the dimensioning and/or operating parameters may include determining convergence criteria for the gas treatment units of the gas treatment plant using an equation-based solution method or sequential-modular solution method for the digital model, wherein the convergence criteria relate to physical system balances. Examples for such balances are those provided by the MESH equations (Material balances, Equilibrium relations, Summation equations, Heat balances) or by the MERSHQ equations (Material balances, Energy balances, mass and heat-transfer Rate equations, Summation equations, Hydraulic equations for pressure drop, eQuilibrium equations) and optionally cost equations for e.g. operational and/or capital expenditures. Here convergence refers to iteratively determining dimensioning and/or operating parameters until convergence criteria are reached in the sense that a threshold value for the physical system balances is reached.

Furthermore providing at least one of the above relative parameters may affect the output in that the output of the operating and/or dimensioning parameters includes the corresponding parameter of the gas treatment unit related to the relative parameter provided as gas treatment unit input parameter. Depending on the relative parameter the operating and/or dimensioning parameters include e.g. the height of the absorber as dimensioning parameter, the diameter of the absorber as dimensioning or the solution flow rate in the absorber under operating conditions as operating parameter. Furthermore, the output of the operating and/or dimensioning parameters includes depending on the relative parameter at least one of the reboiler duty as operating parameter or the regenerator diameter as dimensioning parameter.

In a further embodiment the request to initiate the determination of operating and/or dimensioning parameters in the design or rating case is received from an input unit. Receiving a request to initiate the determination of operating and/or dimensioning parameters may include a data transfer of process specific input parameters and particularly gas treatment unit input parameters from an input unit as sending entity to an interface unit as receiving entity. Here the input unit may be part of a client device and the interface unit may be part of a server. The transfer may be accomplished through a wired or wireless network. In one example, the input unit and the interface unit may be part of a web-based server or cloud system, where the input unit forms the presentation or application layer on the client side and the interface unit forms the interface to underlying layers performing the calculation or determination steps of the method on the server side. The input unit may be implemented as a webservice or a standalone software package. In a further embodiment the input unit, the interface unit, the determination processing unit, optionally the database unit and the output interface may be part of the client device. The input unit may form the presentation or application layer. The interface unit and the output interface may form a communication layer for transferring data between the input unit and the determination processing unit. Optionally the communication layer or a wireless network further facilitates data transfer between the determination processing unit and the database unit.

On the input unit side, the process specific input parameters and particularly gas treatment unit input parameters may be provided according to a permission object. Such permission object may be used for the methods or the input units for generating a request to initiate the determination of operating parameters to operate an existing gas treatment plant or for the methods or the input units for generating a request to initiate the determination of operating and/or dimensioning parameters of a gas treatment plant. The methods or the input units for generating a request to initiate the determination of operating and/or dimensioning parameters of a gas treatment plant relate to a design case, where operating and/or dimensioning parameters of a gas treatment plant to be implemented or physically built are determined. The input units and the methods for generating a request to initiate the determination of operating parameters to operate an existing gas treatment plant particularly relate to a rating case, where operating parameters of an implemented gas treatment plant, which is in operation, are determined. In the rating case the flow rate in the gas treatment unit or the composition specifying a proportion of one or more depleted component(s) in the treated outlet stream may be specified, since the flow rate is a variable parameter in operation of the plant and has direct impact on the composition of the treated outlet stream. In this respect two scenarios may be possible. In one scenario the flow rate may be of interest to be determined for a desired composition which may be provided as gas treatment unit input parameter. In another scenario the desired composition may be of interest to be determined for a desired flow rate which may be provided as gas treatment unit input parameter.

The permission object may define which process specific input parameters and particularly gas treatment unit input parameters are provided as relative parameter or as corresponding parameter, wherein the relative parameter is independent of the plant throughput and relates to at least one corresponding parameter that depends on the plant throughput or the gas treatment unit geometry. Alternatively or additionally the permission object may define which process specific input parameters and particularly gas treatment unit input parameters are provided based on an plant type or an industry application type. Here an industry application type may specify a certain application of the gas treatment plant to be designed and implemented or gas treatment plant in operation. The industry application type may be specified via the purity or composition of the treated outlet stream. In a sales gas application for instance purity grades of less than or equal to 2-4 mol % $CO_2$ in the treated gas may be much lower than in liquified natural gas (LNG) applications with high purity grade requirements of less than or equal to 50 mol ppm $CO_2$ in the treated gas. A minimal set of process specific input parameters may be inlet gas conditions, such as temperature, composition, flow rate and pressure, pressure conditions in the gas treatment units, condensation temperature at the regenerator top and lean solution temperature in the regenerator. In such embodiment all further required specifications may be pre-set. In particular relative parameter(s) may be pre-set rather than corresponding parameter(s). To meet such diverse technical needs, object permissions based on the gas treatment plant type or industry application type can be utilized to restrict process specific input parameters on the input unit level in such a way that the determination of dimensioning and/or operating parameters or the determination of operating parameters to operate an existing gas treatment plant is performed in a controlled and more efficient way.

The permission object(s) may be associated with a pre-defined allowed range for process specific input parameters and particularly gas treatment unit input parameters. For instance, the permission object may define, which process specific input parameters and particularly gas treatment unit input parameters are provided as relative parameter and a pre-defined allowed range in which the relative parameter may lie. For a loading factor, which is defined as set out above with the loading factor of 1 signifying the equilibrium loading with no mass transfer occurring. Such a range may be given by a loading factor $\geq 0.3$ and $\leq 0.98$, preferably $\geq 0.5$ and $\leq 0.95$ and more preferred $\geq 0.6$ and $\leq 0.93$. Such a range may be given by a hydraulic load $\geq 0.2$ and $\leq 0.95$, preferably $\geq 0.4$ and $\leq 0.9$ and more preferred $\geq 0.5$ and $\leq 0.8$, wherein the hydraulic load is determined by the ratio of actual hydraulic load to hydraulic load at flooding limit. Such a range may be given by a strip steam ratio $\geq 0.2$ and $\leq 20$, preferably $\geq 0.5$ and $\leq 10$ and more preferred $\geq 0.7$ and $\leq 5$.

The permission object(s) may be associated with a user profile. Such user profile and the associated permission objects for process specific input parameters may be generated based on registration input provided by the user. For instance, on registration the user provides an industry application type, an advance level such as expert or basic, a task type such as design of a plant to be implemented or rating of a plant that is already operating.

Setting such object permissions on the input unit level allows for enhanced control over the design process in view of the input parameters required for a simplified and more efficient gas treatment plant design or rating. The permission objects set on the input level reduce the solution space in such a way that physically and chemically meaningful operating and/or dimensioning parameters are determined, which when implemented in the physical gas treatment plant lead to stable operation of the gas treatment plant. Moreover, any scenarios resulting in physically and chemically not meaningful or not possible operating and/or dimensioning parameters can be avoided and the number of iterations to reach a meaningful solution is reduced, thus using computer resources in a very efficient way.

Defining which gas treatment unit input parameters are provided as relative parameter or as corresponding parameter, may include for each gas treatment input parameter a permission object allowing to provide a single gas treatment input parameter to be either specified as relative parameter or corresponding parameter or both. The latter option may be implemented by providing on the user interface of the input unit a selection option. Alternatively, the permission object may allow to provide a single gas treatment input parameter to be exclusively specified as relative parameter or as corresponding parameter.

Similarly defining which process specific input parameters are provided based on an industry application type, may include for each process specific and particularly gas treatment input parameter a permission to provide only certain process specific or gas treatment unit input parameters, wherein others are fixed. Alternatively or additionally defining which process specific and particularly gas treatment input parameters are provided based on an industry application type, may include for each gas treatment input parameter a permission to provide only process specific or gas treatment unit input parameters in a specified range.

The input units thus provide the possibility for configuration of the user interface such that the values allowed for input will restrict the possible results to a range that is suitable for the respective application. On the user interface, each process specific input parameter may be reflected via a permission object that defines whether the user can see the respective input field, edit the value of the respective input field, and optionally defines the admitted range for the value. The calculation request may be transferred to e.g. the server, where a further validation step may be performed in which the compliance with the permissions is checked.

Setting permission objects for process specific input parameters and translating those permission objects to the user interface layer, enables customizing the input parameter layer such that the determination of operating and/or dimensioning parameter will firstly converge and secondly will provide chemically and physically meaningful outputs that are directly transferable to the operation of the physical gas treatment plant.

At the input unit side process specific input parameters may be provided in groups. Such groups may be used in methods or input units for generating a request to initiate the determination of operating parameters to operate an existing gas treatment plant or may be used in methods or input units for generating a request to initiate the determination of operating and/or dimensioning parameters of a gas treatment plant. For example, process specific input parameters related to the inlet stream input parameters, the treatment solution or absorption medium input parameters, the gas treatment plant configuration parameters or the gas treatment unit input parameters like the absorber input parameters or the regenerator input parameters may be grouped and optionally displayed separately in accordance with the grouping on the user interface. The grouping of such parameters may further have a hierarchical structure with each group being assigned a dependency or hierarchy level. The dependency or hierarchy level may determine which group on the upper hierarchy level has to be filled with data, e.g. in the sense of providing respective process specific input parameters, as a pre-condition to unlock the next lower hierarchy level. Here unlocking includes for example that the respective group of parameters is activated for input, e.g. via an input mask that becomes visible on a display or input fields that become editable. For further guidance meaningful process specific input parameters and particularly gas treatment unit input parameters which have a direct physical connection may be grouped and displayed in a selectable format. Such direct physical connection is for instance provided by the relative and corresponding parameters, where the specification of one parameter is sufficient to solve the design problem.

In a further example, a first group of process specific input parameters with an assigned first dependency or hierarchy level may inherit elements to a second group of process specific input parameters with an assigned second dependency or hierarchy level, wherein the first dependency or hierarchy level is superordinate to the second dependency or hierarchy level. For instance, the entry of certain gas components in the gaseous inlet stream in the group assigned the first hierarchy level may trigger a further input on the absorption medium in the group assigned the second hierarchy level.

The interface unit and the database unit may be in communication with the determination processing unit. The determination processing unit is configured to initialize the digital model based on the process specific input parameters and e.g. the thermodynamic parameters and to determine a solution for the unit operations of the gas treatment plant via the sequential-modular solution approach or when represented in a system of equations using an equation-based solution method, wherein the solution specifies the operating and/or dimensioning parameters.

In a further embodiment, the output interface is in communication to the determination processing unit providing the operating and/or dimensioning parameters including e.g. the corresponding parameters of the gas treatment unit related to the at least one relative parameter provided as gas treatment unit input parameter.

In a further embodiment the determined operating and/or dimensioning parameters are communicated to an engineering system, which implements the operating and/or dimensioning parameters into a design system for a full plant process flowsheet simulation tool, where the gas treatment plant is a part of, and/or into a physical design of the gas treatment plant to be built. Thus, the determination of operating and/or dimensioning parameters may be embedded into an overall process plant design including in addition to a gas treatment plant, such as an acid gas removal plant, further steps such as dehydration processes, liquefaction processes, sulfur recovery unit, steam reformer, methanizer, partial oxidation unit, ammonia reactor and recycling streams. The determination of dimensioning and/or operating parameters may be performed on the design system for a full plant process flowsheet simulation tool embedded on one client device. Alternatively, the determination of dimensioning and/or operating parameters may be performed on a server and the dimensioning and/or operating parameters may be transferred via e.g. a wireless network to the design system on a client device or on another server. This allows for a seamless integration of the process specific operating conditions from a chemical engineering perspective into further design steps such as the mechanical engineering step or the construction step. After the full design is completed the gas treatment plant as designed goes into physical construction implementing the determined operating and/or dimensioning parameters.

Additionally the methods for determining operating and/or dimensioning parameters for gas treatment plants may be used in training operating personnel or in a rigorous model based advanced process control. In case of training the methods may be connected to an operation stand and from any input by the personnel to the operation stand process specific input parameters may be generated. Based on such generated input parameters operating and/or dimensioning parameters may be determined and a feedback may be given to the operator. In case of rigorous model based advanced process control the software is run in rating mode. Based on process specific input parameters operating parameters may be determined and compared to measured operating parameters in real time.

In an further embodiment of the present invention, a method for determining operating and/or dimensioning parameters of a gas treatment plant for treating a gaseous inlet stream with a treatment solution to provide a treated outlet stream including one or more gas treatment units comprises: receiving, by a processing device, a request to initiate the determination of operating and/or dimensioning parameters of the gas treatment plant, wherein the request comprises gas treatment unit input parameters for the one or more gas treatment unit(s), wherein the gas treatment unit input parameters include at least one relative parameter which is independent of the plant throughput; initializing, by the processing device, a digital model of the gas treatment plant based on the gas treatment unit input parameters and including a relation of the at least one relative parameter to a corresponding parameter, wherein the corresponding parameter is dependent on the plant throughput or dependent on a gas treatment unit geometry and is a result of the relation to the at least one relative parameter, wherein the digital model characterizes the mass and heat transfer in the gas treatment plant including one or more gas treatment unit(s); determining, by the processing device, operating and/or dimensioning parameters of the gas treatment plant including the corresponding parameter based on the digital model; and outputting, by the processing device, the operating and/or dimensioning parameters including the corresponding parameter dependent on the plant throughput or dependent on the gas treatment unit geometry.

In a further embodiment real time notifications are provided via the determination and/or output unit, while the operating and/or dimensioning parameters of the gas treatment plant are determined. Since the digital model is solved iteratively, such notifications provide real-time status updates to a user e.g. on the level of convergence or the progress of the determination.

In one embodiment the interface unit, the determination processing unit, the database unit and the output interface are part of a server, wherein the interface unit and the output interface are in communication to a client device. The request to initiate the determination of operating and/or dimensioning parameters of the gas treatment plant may be triggered by the client device. Outputting the operating and/or dimensioning parameters may include sending the operating and/or dimensioning parameters to the client device. In case of real time notifications, it may also be the determination processing unit, which is in communication with the client device.

In one embodiment, a method may include designing and assembling a gas treatment plant based on the operating and/or dimensioning parameters determined by one or more of the methods described herein. In another embodiment, a method may include treating a gas stream using the gas treatment plant.

It is to be understood that the embodiments described herein are not mutually exclusive of each other, and that one or more of the described embodiments may be combined in various ways, as would be appreciated by one of ordinary skill in the art.

According to another aspect of the present invention, a computer program product is provided comprising computer-readable instructions which, when loaded and executed on processor, perform the method according to any one of the embodiments of the first aspect or the first aspect as such.

A computer program performing any of the methods of the present invention may be stored on a computer-readable storage medium (e.g., a non-transitory computer-readable storage medium). A computer-readable storage medium may be a floppy disk, a hard disk, a CD (Compact Disk), a DVD (Digital Versatile Disk), a USB (Universal Serial Bus) storage device, a RAM (Random Access Memory), a ROM (Read Only Memory), an EPROM (Erasable Programmable Read Only Memory), or other suitable device. The present invention can be implemented in digital electronic circuitry, or in computer hardware, firmware, software, or in combinations thereof, e.g. in available hardware of conventional mobile devices or in new hardware dedicated for processing the methods described herein, as will be described in greater detail below.

BRIEF DESCRIPTION OF THE DRAWINGS

Exemplary embodiments of the present invention are illustrated in the appended drawings. It is to be noted, however, that the appended drawings illustrate only particular embodiments of the present invention and are therefore not to be considered limiting of its scope. The present invention may encompass other equally effective embodiments.

FIG. 5 shows an exemplary embodiment of a graphical user interface to generate the process specific input parameters for the method;

DETAILED DESCRIPTION OF EMBODIMENTS

Figure 1:
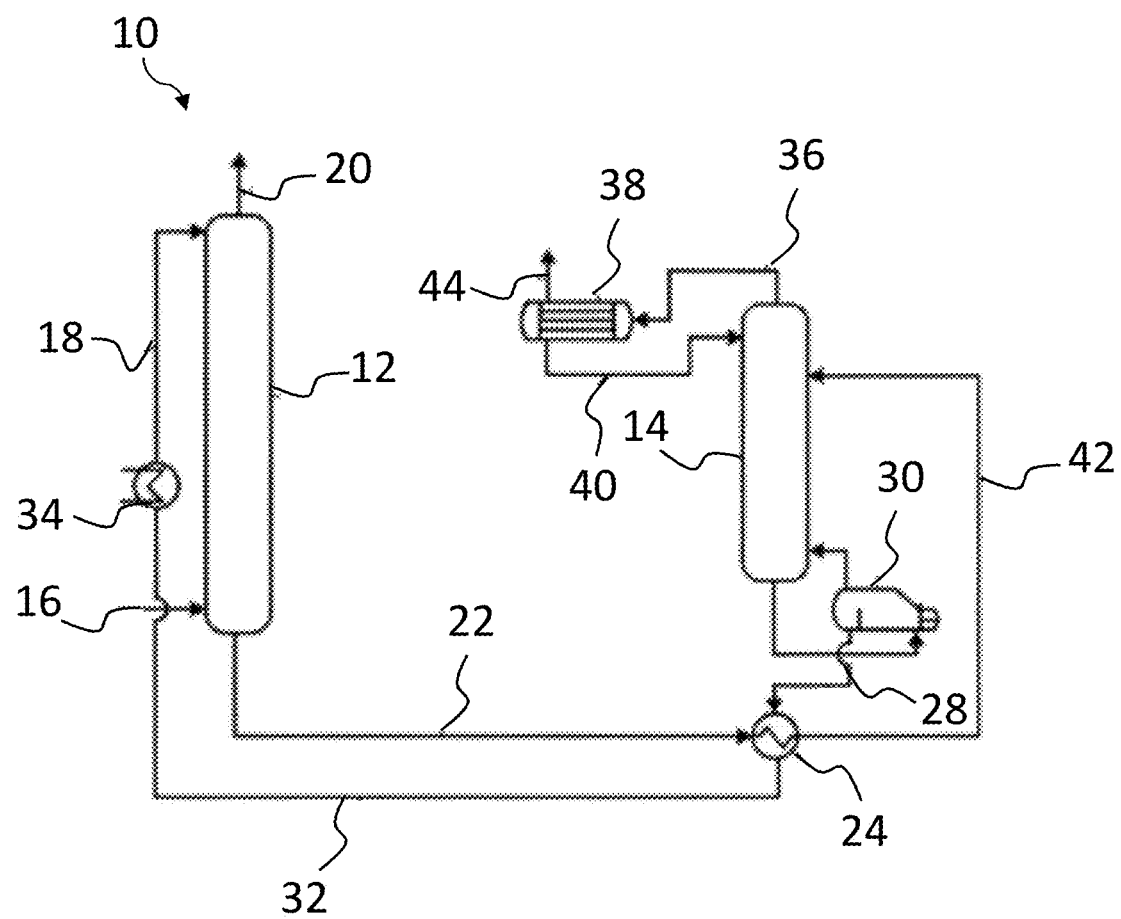
FIG. 1 shows an exemplary flowsheet of an acid gas removal plant including one absorber-regenerator cycle.

FIG. 1 shows an exemplary flowsheet of an acid gas removal plant 10 including one absorber-regenerator cycle, The flowsheet is defined by the combination of single unit operations or gas treatment units, like mixer, heater/cooler, flash stage, equilibrium stage column and rate based column. The single unit operations are connected by streams or interconnections. Recycle streams or interconnections may be present which lead to the fact that changes in one unit operation have an impact on some or all unit operations in the flowsheet.

The acid gas removal plant 10 of FIG. 1 includes an absorber 12 and a desorption column 14 as regenerator for the treatment solution. The treatment solution may include an aqueous amine solution as absorption medium. Absorption mediums comprise at least one amine. The following amines are preferred:

(i) amines of formula I:

$$NR^1(R^2)_2 \qquad (I)$$

where R1 is selected from C2-C6-hydroxyalkyl groups, C1-C6-alkoxy-C2-C6-alkyl groups, hydroxy-C1-C6-alkoxy-C2-C6-alkyl groups and 1-piperazinyl-C2-C6-alkyl groups and R2 is independently selected from H, C1-C6-alkyl groups and C2-C6-hydroxyalkyl groups;

(ii) amines of formula II:

$$R^3R^4N{-}X{-}NR^5R^6 \qquad (II)$$

where R3, R4, R5 and R6 are independently of one another selected from H, C1-C6-alkyl groups, C2-C6-hydroxyalkyl groups, C1-C6-alkoxy-C2-C6-alkyl groups and C2-C6-aminoalkyl groups and X represents a C2-C6-alkylene group, —X1-NR7-X2- or —X1-O—X2-, where X1 and X2 independently of one another represent C2-C6-alkylene groups and R7 represents H, a C1-C6-alkyl group, C2-C6-hydroxyalkyl group or C2-C6-aminoalkyl group;

(iii) 5- to 7-membered saturated heterocycles which have at least one nitrogen atom in the ring and may comprise one or two further heteroatoms selected from nitrogen and oxygen in the ring, and (iv) mixtures thereof.

Specific examples are:

(i) 2-aminoethanol (monoethanolamine), 2-(methylamino)ethanol, 2-(ethylamino)ethanol, 2-(n-butylamino)ethanol, 2-amino-2-methylpropanol, N-(2-aminoethyl)piperazine, methyldiethanolamine, ethyldiethanolamine, dimethylaminopropanol, t-butylaminoethoxyethanol, 2-amino-2-methylpropanol;

(ii) 3-methylaminopropylamine, ethylenediamine, diethylenetriamine, triethylenetetramine, 2,2-dimethyl-1,3-diaminopropane, hexamethylenediamine, 1,4-diaminobutane, 3,3-iminobispropylamine, tris(2-aminoethyl)amine, bis(3-dimethylaminopropyl)amine, tetramethylhexamethylenediamine;

(iii) piperazine, 2-methylpiperazine, N-methylpiperazine, 1-hydroxyethylpiperazine, 1,4-bishydroxyethylpiperazine, 4-hydroxyethylpiperidine, homopiperazine, piperidine, 2-hydroxyethylpiperidine and morpholine; and (iv) mixtures thereof.

In a preferred embodiment the absorption medium comprises at least one of the amines monoethanolamine (MEA), methylaminopropylamine (MAPA), piperazine, diethanolamine (DEA), triethanolamine (TEA), diethylethanolamine (DEEA), diisopropylamine (DIPA), aminoethoxyethanol (AEE), dimethylaminopropanol (DIMAP) and methyldiethanolamine (MDEA) or mixtures thereof.

The amine is preferably a sterically hindered amine or a tertiary amine. A sterically hindered amine is a secondary amine in which the amine nitrogen is bonded to at least one secondary carbon atom and/or at least one tertiary carbon atom; or a primary amine in which the amine nitrogen is bonded to a tertiary carbon atom. One preferred sterically hindered amine is t-butylaminoethoxyethanol. One preferred tertiary amine is methyldiethanolamine When the amine is a sterically hindered amine or a tertiary amine the absorption medium preferably further comprises an activator. The activator is generally a sterically unhindered primary or secondary amine. In these sterically unhindered amines the amine nitrogen of at least one amino group is bonded only to primary carbon atoms and hydrogen atoms.

The sterically unhindered primary or secondary amine is, for example, selected from alkanolamines, such as monoethanolamine (MEA), diethanolamine (DEA), ethylaminoethanol, 1-amino-2-methylpropan-2-ol, 2-amino-1-butanol, 2-(2-aminoethoxy)ethanol and 2-(2-aminoethoxy)ethanamine, polyamines, such as hexamethylenediamine, 1,4-diaminobutane, 1,3-diaminopropane, 3-(methylamino)propylamine (MAPA), N-(2-hydroxyethyl)ethylenediamine, 3-(dimethylamino)propylamine (DMAPA), 3-(diethylamino)propylamine, N,N'-bis(2-hydroxyethyl)ethylenediamine, 5-, 6- or 7-membered saturated heterocycles which have at least one NH group in the ring and may comprise one or two further heteroatoms selected from nitrogen and oxygen in the ring, such as piperazine, 2-methylpiperazine, N-methylpiperazine, N-ethylpiperazine, N-(2-hydroxyethyl)piperazine, N-(2-aminoethyl)piperazine, homopiperazine, piperidine and morpholine.

Particular preference is given to 5-, 6- or 7-membered saturated heterocycles which have at least one NH group in the ring and may comprise one or two further heteroatoms selected from nitrogen and oxygen in the ring. Very particular preference is given to piperazine.

In one embodiment the absorption medium comprises methyldiethanolamine and piperazine.

The molar ratio of activator to sterically hindered amine or tertiary amine is preferably in the range from 0.05 to 1.0, particularly preferably in the range from 0.05 to 0.7.

The absorption medium generally comprises 10% to 60% by weight of amine.

The absorption medium is preferably aqueous.

The absorption medium may further comprise a physical solvent. Suitable physical solvents are, for example, N-methylpyrrolidone, tetramethylenesulfone, methanol, oligoethylene glycol dialkyl ethers such as oligoethylene glycol methyl isopropyl ether (SEPASOLV MPE), oligoethylene glycol dimethyl ether (SELEXOL). The physical solvent is generally present in the absorption medium in amounts of 1% to 60% by weight, preferably 10% to 50% by weight, in particular 20% to 40% by weight.

In a preferred embodiment the absorption medium comprises less than 10% by weight, for example less than 5% by weight, in particular less than 2% by weight of inorganic basic salts, such as potassium carbonate for example.

The absorption medium may also comprise additives, such as corrosion inhibitors, antioxidants, enzymes etc. In general, the amount of such additives is in the range of about 0.01-3% by weight of the absorption medium.

Further examples of absorption mediums are (1-1) aqueous solution of methyldiethanolamine (MDEA) (2.2 M) and piperazine (1.5 M); (1-2) aqueous solution of 2-(2-tertbutylaminoethoxy)ethanol (TBAEE) (2.2 M) and piperazine (1.5 M); and (1-3) aqueous solution of 2-(2-tert-butylaminoethoxy)ethanol (TBAEE) (2.2 M) and monoethanolamine (MEA) (1.5 M). With the absorption mediums listed above acid gas removal of e.g. $CO_2$, $H_2S$, $SO_2$, $CS_2$, HCN, COS or mercaptans is possible. Other applications consider absorption of alcohols, acetone and/or organic acids in water, ethylene oxide in water, ammonia in water, water vapor in di- or triethylene glycol, hydrocarbons in high boiling organic solvents, HF, HCl, HBr, HI in water, NOx in $H2O/HNO3$ or $SO2$ in alkaline solution.

According to FIG. 1, via the inlet 16, a suitably pretreated gaseous inlet stream comprising carbon dioxide ($CO_2$) and/or hydrogen sulfide ($H_2S$) is contacted in countercurrent, in an absorber 12, with regenerated absorption medium which is fed in the absorber 12 via the absorption medium line 18. The absorption medium removes carbon dioxide and/or hydrogen sulfide from the gas inlet stream by absorption. This results in a carbon dioxide- and/or hydrogen sulfide-depleted clean outlet gas via the offgas line 20.

Via the absorption medium line 22, the heat exchanger 24 in which the $CO_2$- and/or $H_2S$-laden absorption medium is heated up with the heat from the regenerated absorption medium conducted through the absorption medium line 28. Via the absorption medium line 42, the $CO_2$- and/or $H_2S$-laden absorption medium is fed to the desorption column 14 and regenerated. From the lower part of the desorption column 14, the absorption medium is conducted into the reboiler 30, where it is heated and partly evaporated. The mainly water-containing vapor is recycled into the desorption column 14, while the regenerated absorption medium is fed back to the absorber 12 via the absorption medium line 28, the heat exchanger 24, the absorption medium line 32, the cooler 34 and the absorption medium line 18. In the heat exchanger 24 the regenerated absorption medium heats up the $CO_2$- and/or $H_2S$-laden absorption medium and at the same time cools down itself.

Instead of the boiler 30 shown, it is also possible to use other heat exchanger types to raise the stripping vapor, such as a natural circulation evaporator, forced circulation evaporator or forced circulation flash evaporator. In the case of these evaporator types, a mixed-phase stream of the regenerated absorption medium and stripping vapor is returned to the bottom of the desorption column 14, where the phase separation between the vapor and the absorption medium takes place. The regenerated absorption medium to the heat exchanger 24 is either drawn off from the circulation stream from the bottom of the desorption column 14 to the evaporator or conducted via a separate line directly from the bottom of the desorption column 14 to the heat exchanger 24.

The $CO_2$- and/or $H_2S$-containing gas released in the desorption column 14 leaves the desorption column 14 via the offgas line 36. It is conducted into a condenser 38 with integrated phase separation, where it is separated from entrained absorption medium vapor. Subsequently, a liquid consisting mainly of water is conducted through the absorption medium line 40 into the upper region of the desorption column 14, and a $CO_2$- and/or $H_2S$-containing gas is discharged via the gas line 44.

The flowsheet of FIG. 1 illustrates a gas treatment plant 10 including gas treatment units 12, 14 and may be used as a basis to provide the gas treatment plant configuration parameters, which are provided as part of the process specific input parameters for performing the methods for determining operating and/or dimensioning parameters.

Figure 2:
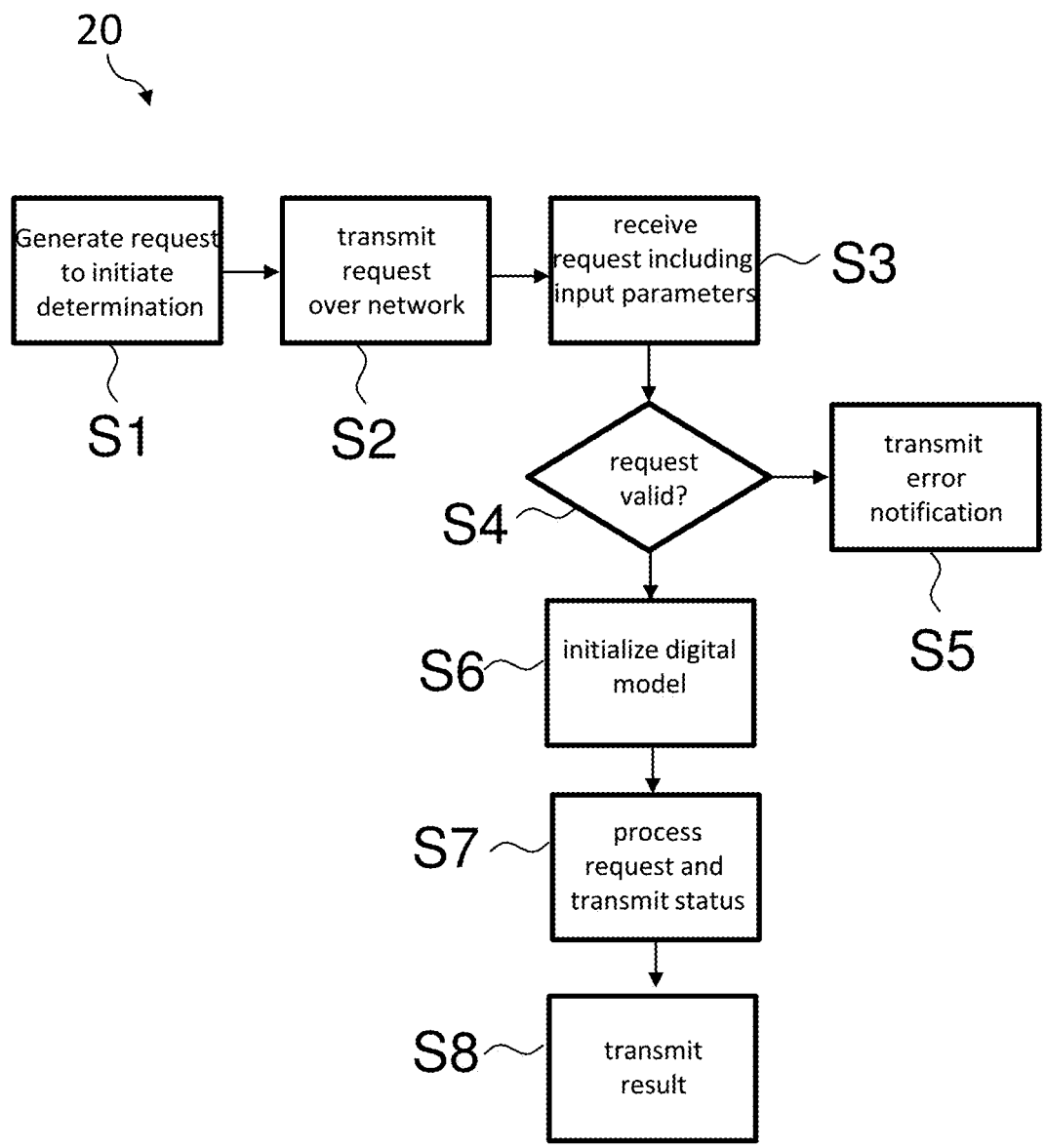
FIG. 2 shows an exemplary embodiment of the method for determining operating and/or dimensioning parameters of a gas treatment plant in a client-server set-up.

FIG. 2 shows a schematic flowchart diagram of the method 20 for determining operating and/or dimensioning parameters of a gas treatment plant 10 according to an exemplary embodiment of the present invention.

The method 20 for determining operating and/or dimensioning parameters of a gas treatment plant 10 may comprise at least the following steps:

As a first step of the method 20, generating S1 a request to initiate the determination of operating and/or dimensioning parameters of the gas treatment plant 10 is performed. The request comprises process specific input parameters including absorber input parameters. The absorber input parameters include at least one of the absorber height or the solution flow rate as corresponding input parameter. Hence it may not be the absorber height that is specified, but rather the composition in the treated outlet stream. Similarly, it may not be flow rate that is specified, but rather the loading factor of the treatment solution in the absorber 12. In specifying relative parameters different scenarios exist. In one example the absorber input parameters may include the composition in the treated outlet stream and the loading factor of the treatment solution in the absorber 12. In another example the absorber input parameters may include the composition in the treated outlet stream and flow rate. In yet another example the absorber input parameters may include the absorber height and the loading factor of the treatment solution in the absorber 12.

In another embodiment the absorber input parameters further include the absorber diameter as relative parameter. In this embodiment at least one of the absorber height, the solution flow rate or the absorber diameter are provided as relative parameter. Here different scenarios are possible:
- only one parameter, namely the absorber height, the solution flow rate or the absorber diameter, is provided as relative parameter,
- two parameters are provided as relative parameters, e.g. the absorber height and the solution flow rate or the absorber height and the absorber diameter or the solution flow rate and the absorber diameter, or
- all three parameters, namely the absorber height, the solution flow rate and the absorber diameter, are provided as relative parameter.

The absorber input parameters may further include configuration parameters specifying the absorber's internal configuration. Such configuration parameters may further specify the column type such as packed bed or tray column, the number of segments indicating the height discretization in the column, pressure conditions like the pressure drop over the column, temperature conditions or a distributor type for the liquid treatment solution.

The process specific input parameters may further include inlet stream specific parameters such as the composition, the molar flow rate, temperature, pressure or the like, treatment solution parameters such as the composition, grade, strength or the like. If further gas treatment units such as a regenerator are present, the process specific input includes further parameters specifying each of the gas treatment units. Alternatively, some of the parameters specifying further gas treatment units may be pre-set to simplify and reduce the number of process specific input parameters to be provided.

The gas treatment plant 10 may include more than one absorber and/or further gas treatment units, as for instance shown in FIG. 1 with absorber 12, regenerator 14, cooler 34, heat exchanger 24, reboiler 30 and condenser 38. Preferably, the process specific input parameters include configuration parameters, which specify the gas treatment units included in the gas treatment plant 10 and their interconnection. These may be partly or fully pre-defined providing a fixed set of possible configurations. Such pre-defined configurations may be stored in a database and can be identified in the process specific input parameters via identifiers signifying the respective configurations. Pre-defined configurations simplify the design process for the user by reducing the number of viable options. Moreover, it leads to a more robust and stable determination of operating and/or dimensioning parameters, since non-sensible or technically meaningless specifications are excluded. Where the configurations are only partly or not pre-defined the method 20 can include a validation to ensure sensible configurations are provided. Such a validation for instance checks that all required gas treatment units are included, that all interconnections between the gas treatment units are present, that no fault interconnections between the gas treatment units are present or that the gas treatment units are interconnected in accordance with their function. Such validation may be implemented in a rule-based manner.

If the gas treatment plant 10 also includes a regenerator as for instance shown in FIG. 1, the process specific input parameters further comprise regenerator input parameters including at least one of the reboiler duty or the regenerator diameter as relative parameters. Hence for the reboiler duty it may not be the reboiler duty that is specified, but the fraction quality of the regenerated treatment solution or strip steam ratio. Similarly, for the regenerator diameter it may not be the regenerator diameter that is specified, but the acceptable hydraulic load. In specifying relative parameters different scenarios exist. In one example the regenerator input parameters may include the fraction quality of the regenerated treatment solution or strip steam ratio and the acceptable hydraulic load. In another example the regenerator input parameters may include the fraction quality of the regenerated treatment solution or strip steam ratio and the regenerator diameter. In yet another example the regenerator input parameters may include the reboiler duty and the acceptable hydraulic load.

In a further embodiment the regenerator input parameters include configuration parameters specifying the regenerator configuration. Such configuration parameters may further specify the regenerator column type such as packed bed or tray column, the number of segments in the column, pressure conditions like the pressure drop over the column or temperature conditions.

With the relative parameters available for the absorber input parameters and for the regenerator input parameters all combinations are possible. Depending on the user profile all or only a subset of options may be available to the user. The process specific input parameters may thus include all of the available absorber and regenerator input paraments in relative form. Alternatively only a sub-set of the available absorber and regenerator input paraments are provided in relative form.

As a second step of the method 20, transmitting S2 the generated request over a network may be performed. Here the requested generated at the input unit may be transmitted from the client device to the server via a wireless or wired network. On the server side, the request is received S3 in a third step. On receipt of the request, the validity of the request is checked S4. Here particularly, compliance with the object permissions for the process-specific parameters associated with the user profile are validated. If the request is not valid an error message or notification is transmitted S5 from the server to the client device.

If the request is valid, the digital model based on the process specific input parameters and the thermodynamic parameters is initialized S6. The digital model represents the gas treatment units of the gas treatment plant 10. The digital model includes models for each gas treatment unit of the gas treatment plant 10 such as an absorber model and a regenerator model. The model comprises thermodynamic equations indicative of the thermodynamic conditions such as the mass and energy transfer present in the respective gas treatment unit, which refers to the unit operations implemented in the gas treatment plant 10. The equations are combined in a single system of equations including all the equations for all gas treatment units present in the gas treatment plant 10. For each relative parameter specified in the process specific input parameters the system of equations includes further equations taking account of the relation between the relative parameter and the respective corresponding parameter. This allows to release the respective corresponding parameter and to leave it to the determination of the operating and/or dimensioning parameters.

Depending on the relative parameters provided via the process specific input parameters the digital model of the gas treatment plant is initialized S7 accordingly. For each relative parameter provided via the process specific input parameters the digital model includes a relation between the relative and the corresponding parameter to release the corresponding parameter in the equation-based solution method. In other words, for each relative parameter the system of equations will include an additional equation allowing to release the corresponding parameter.

In step S7 the request is processed based on the initialized digital model and operating and/or dimensioning parameters are calculated iteratively in an equation-based solution approach until convergence criteria are met. During such calculation status notifications may be transmitted from the server to the client device allowing the user to follow the progress of the calculation.

Lastly, the operating and/or dimensioning parameters resulting from such processing are transmitted S8 from the server to the client device.

Figure 3:
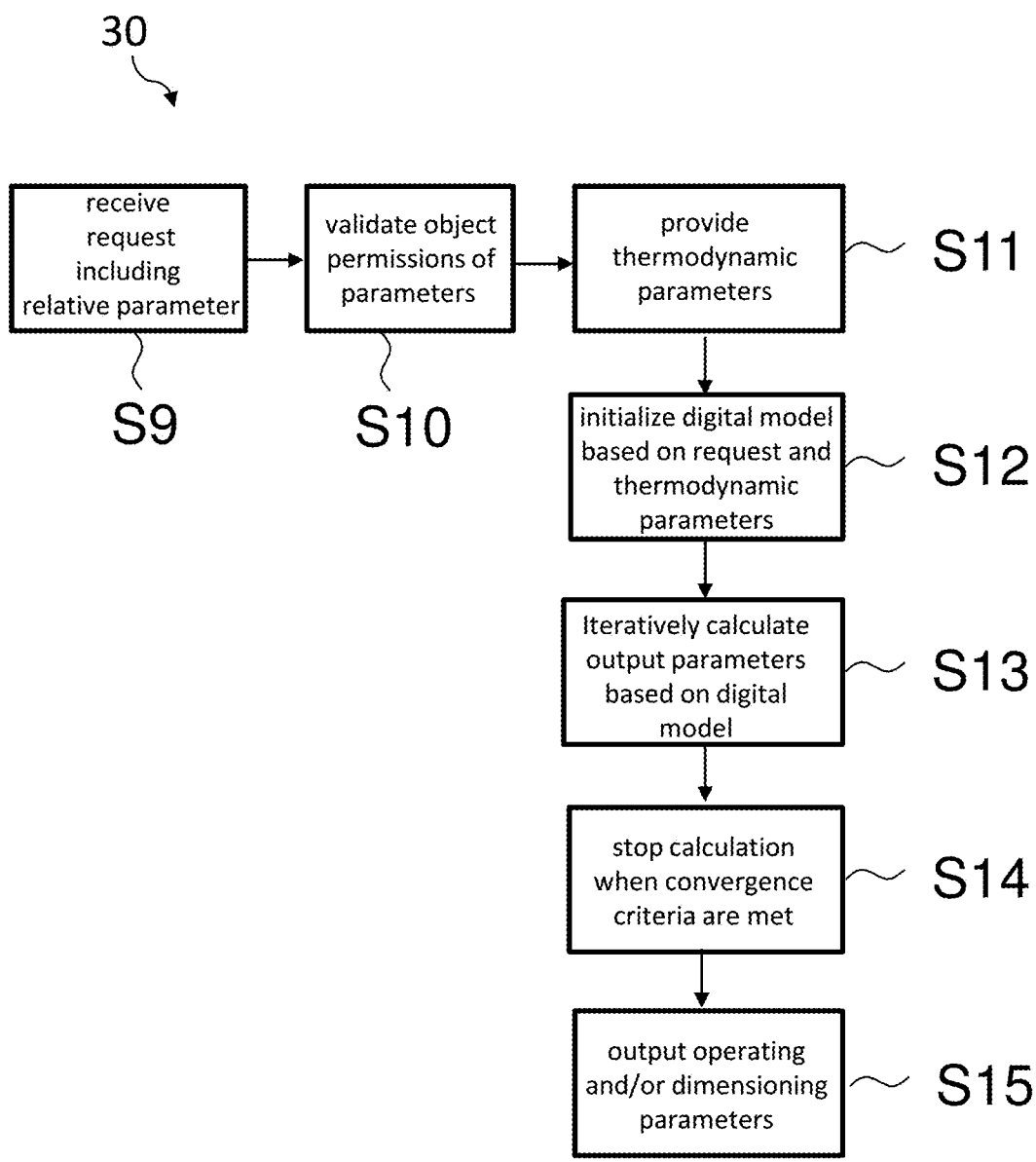
FIG. 3 shows a further exemplary embodiment of the method for determining operating and/or dimensioning parameters of a gas treatment plant.

FIG. 3 shows a schematic flowchart diagram of the method 30 for determining operating and/or dimensioning parameters of a gas treatment plant 10 according to a further exemplary embodiment of the present invention.

In step S9 the request to initiate the determination of operating and/or dimensioning parameters of the gas treatment plant is received. The request comprises process specific input parameters including gas treatment unit input parameters. The gas treatment unit input parameters include at least one relative parameter which is independent of the plant throughput, wherein the relative parameter relates to at least one corresponding parameter dependent on the plant throughput. In a specific embodiment the request comprises process specific input parameters including absorber input parameters, wherein the absorber input parameters include a loading factor of the treatment solution in the absorber as relative parameter.

On receipt of the request, the validity of the request is checked S10. Here particularly, compliance with the object permissions of the process-specific parameters are validated. If the request is valid, thermodynamic parameters indicative of thermodynamic properties in the gas treatment plant 10 under operating conditions are provided S11. Such database access complements the input file and as such simplifies the design process. The thermodynamic parameters are indicative of thermodynamic properties in gas treatment units such as the absorber 12 under operating conditions. The data may be stored in a database unit and complements the process specific input parameters. Based on historical measurement data, e.g. as measured for gas treatment plants 10 in operation or in experimental set-ups, the thermodynamic parameters may provide a viable model base for e.g. thermodynamic absorption medium-gas parameters or kinetic parameters. Including such parameters based on historical measurement data increases the accuracy of the method and reduces the number of parameters to be provided via the process specific input parameters.

If the request is valid, the digital model based on the process specific input parameters and the thermodynamic parameters is initialized S12. The digital model represents the gas treatment units of the gas treatment plant 10. The digital model includes models for each gas treatment unit of the gas treatment plant 10 such as an absorber model and a regenerator model. The model comprises thermodynamic equations indicative of the thermodynamic conditions such as the mass and energy transfer present in the respective gas treatment unit, which refers to the unit operations implemented in the gas treatment plant 10. The equations are combined in a single system of equations including all the equations for all gas treatment units present in the gas treatment plant 10. For each relative parameter specified in the process specific input parameters the system of equations includes further equations taking account of the relation between the relative parameter and the respective corresponding parameter. This allows to release the respective corresponding parameter and to leave it to the determination of the operating and/or dimensioning parameters.

Depending on the relative parameters provided via the process specific input parameters the digital model of the gas treatment plant is initialized S12 accordingly. For each relative parameter provided via the process specific input parameters the digital model includes a relation between the relative and the corresponding parameter to release the corresponding parameter in the equation-based solution method. In other words, for each relative parameter the system of equations will include an additional equation allowing to release the corresponding parameter.

In step S13 operating and/or dimensioning parameters are calculated iteratively in an equation-based solution approach based on the initialized digital model. During such calculation status notifications may be transmitted from the server to the client device allowing the user to follow the progress of the calculation.

In step S14 the calculation of operating and/or dimensioning parameters is stopped, if convergence criteria are met. The convergence criteria relate to physical system balances. Examples for such balances are those provided by the MESH equations (Material balances, Equilibrium relations, Summation equations, Heat balances) or by the MERSHQ equations (Material balances, Energy balances, mass and heat-transfer Rate equations, Summation equations, Hydraulic equations for pressure drop, eQuilibrium equations) and optionally cost equations for e.g. operational and/or capital expenditures. Here convergence refers to iteratively determining dimensioning and/or operating parameters until convergence criteria are reached in the sense that a threshold value for the physical system balances is reached.

In step S15 the operating and/or dimensioning parameters according to the converged calculation are output. The operating and/or dimensioning parameters include depending on the relative input parameters the absorber height, the absorber diameter, the treatment solution flow rate, the reboiler duty and/or the regenerator diameter. The operating and/or dimensioning parameters include, if only a sub set of the available input parameters are provided as relative parameters, the corresponding sub-set of corresponding parameters.

Figure 4:
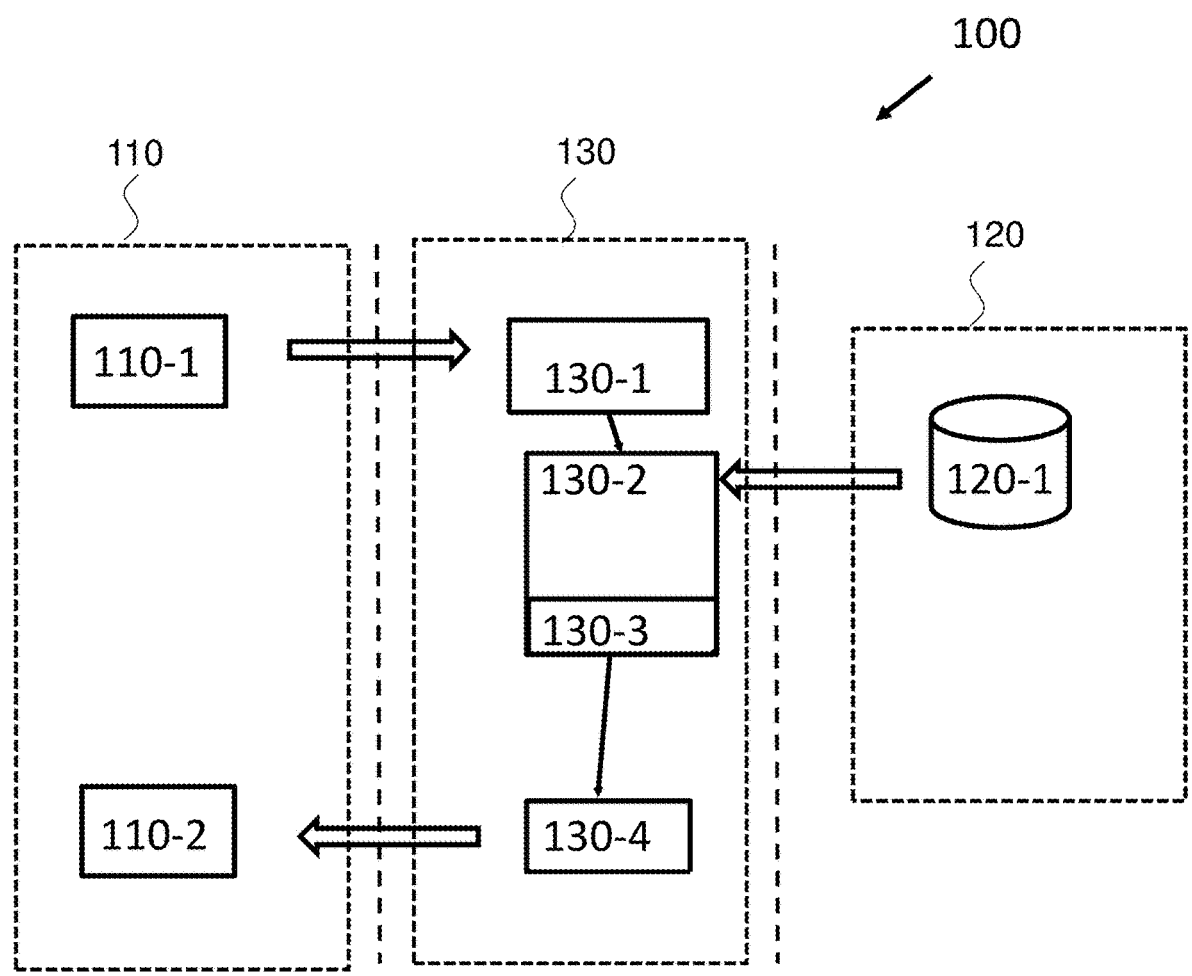
FIG. 4 shows an exemplary embodiment of the system for determining operating and/or dimensioning parameters of a gas treatment plant.

FIG. 4 shows a schematic diagram of a system for determining operating and/or dimensioning parameters of a gas treatment plant 10 according to an exemplary embodiment of the present invention.

The system 100 for determining operating and/or dimensioning parameters of a gas treatment plant 10 comprises a client device 110, a database server 120, and a determination server 130.

The client device 110 includes an input unit 110-1 that is configured to generate process specific input parameters. Such parameters may be provided by a user or pre-set but still editable by the user. The client device 110 sends the request to initiate the determination of operating and/or dimensioning parameters to the determination server 130. The request is send via a wired or wireless network such as a Local Area Networks (LAN) and includes the process specific input parameters.

On the receiver side the determination server 130 comprises the interface unit 130-1, the determination processing unit 130-2 and the output interface 130-4. The interface unit 130-1 is configured to receive the request initiating the determination of operating and/or dimensioning parameters. The data base server 120 comprising the database unit 120-1 is configured to provide thermodynamic parameters indicative of thermodynamic properties in the gas treatment plant 10 under operating conditions. The thermodynamic parameters may be based on historical measurement data.

The determination processing unit 130-2 is in communication with the database unit 120-1 and the interface unit 130-1 and is configured to initialize the digital model based on the process specific input parameters and the thermodynamic parameters. The determination processing unit 130-2 is further configured to determine operating and/or dimensioning parameters of the gas treatment plant 10 using the equation-based solution method for the digital model. Determining the such parameters is done iteratively until convergence criteria are reached and real-time status may be provided to the client device 110.

The output interface 130-4 is configured to output the operating and/or dimensioning parameters including corresponding parameters depending on the corresponding dimensionless input parameter as described above. The determined operating and/or dimensioning parameters received from the calculation unit 130-2 are send to the client device 110 via a wired or wireless network such as a Local Area Networks (LAN) from the output interface 130-4. On the client device 110 side a display unit 110-2 may output the result to a user or may act as an interface providing the result to further engineering devices.

FIG. 5 shows an exemplary embodiment of a graphical user interface 200 to generate the process specific input parameters for the method.

For specification of equipment dimensions and process conditions the input unit 110-1 includes an input display 200. For guidance of the user the input display 200 provides process specific input parameters in groups 210. For example, process specific input parameters related to the inlet stream input parameters, the absorption medium input parameters, the gas treatment plant configuration parameters 220 or the gas treatment unit input parameters like the absorber input parameters 230 or the regenerator input parameters are grouped and displayed separately in accordance with the grouping.

The grouping of such parameters may further have a hierarchical structure with each group being assigned a dependency or hierarchy level. The dependency or hierarchy level may determine which group on the upper hierarchy level has to be filled with data, e.g. in the sense of providing respective process specific input parameters, as a pre-condition to unlock the next lower hierarchy level. Here unlocking includes the respective group of parameters being activated for input, e.g. via the input mask 240 that becomes visible on a display or input fields that become editable. As for instance shown in FIG. 5, the group relating to the absorber input parameters 230 are unlocked only when the group of gas treatment plant configuration parameters 220 is filled with respective data. In FIG. 5 the group relating to the gas treatment unit input parameters is labelled units including the sub-groups absorber 230, flash, regenerator and heat exchangers. Such a grouping with hierarchical structure on the input unit 110-1 side provides user guidance and avoids errors in providing the process specific input parameters.

For further guidance meaningful parameters which have a direct physical connection on one design value may be grouped and displayed in a selectable format such as a drop-down list or as shown in FIG. 5 via a selectable box. For example, in case of the absorber input parameter the input mask 240 includes the solution flow rate specification 280 that can be defined by a value for the mass or volume flow rate or preferably by the loading factor.

With this structure the user input unit 110-1 gives guidance to the user in the design phase of a gas treatment plant design to specify only physically meaningful parameters, which have a direct impact on the process values. Due to the grouping of specifications in the input, the method is very easy to use. Applying the method to create a gas treatment plant design the designer will specify a set of physically meaningful input parameters so that the result gives already the desired result after one step of user input, which reduces the required time for the design procedure significantly.

As example, a preferred set of standard specifications of the absorber 12 referenced to as dimensionless specifications could be
- to specify 270 the concentration of $CO_2$ or $H_2S$ in the treated gas to calculate the absorber height,
- to specify 250 the acceptable hydraulic load (distance to hydraulic flooding conditions or safety factor) to calculate the absorber diameter and
- to specify 280 the maximum $CO_2/H_2S$ loading factor or maximum combined $CO_2+H_2S$ loading factor to calculate the solution flow rate.

Additionally the solution temperature, the temperature difference between absorber inlet and outlet or the transferred heat in the absorber may be specified 260. For the regeneration the required quality of the key component in the regenerator or stipper bottom stream or lean solution to calculate the reboiler duty can be specified in the input mask 240 which belongs to the group of regenerator input parameters.

The method uses an equation-oriented solution approach, which allows this approach of dimensionless specifications. One example of the dimensionless specifications is the implementation to release the column height. Thus, the absorber height can be calculated as result of another connected specifications like the acid gas content in the treated gas.

Figure 6:
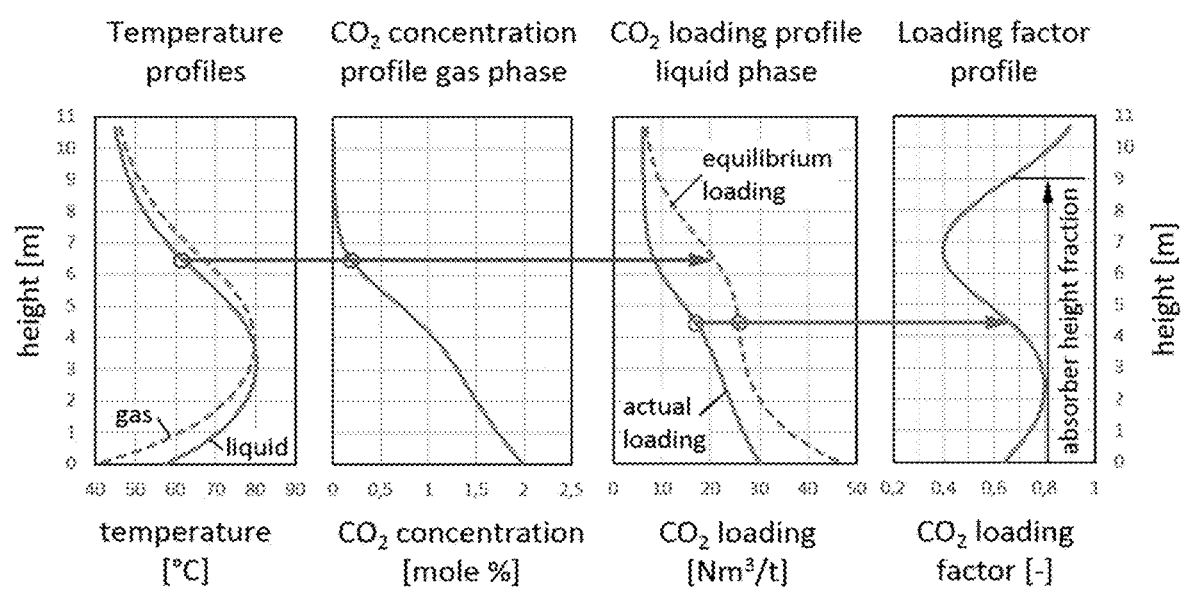
FIG. 6 illustrates an exemplary embodiment for determining the $CO_2$ loading factor via the ratio of the actual loading to the equilibrium loading in the liquid phase.

FIG. 6 illustrates an exemplary embodiment for determining the $CO_2$ loading factor via the ratio of the actual loading to the equilibrium loading in the liquid phase.

One element for allowing the relative parameters is to provide the loading factor at the absorber bottom or the maximum loading factor along the absorber height. Exemplary column profiles to determine the loading factor are shown in FIG. 6. The first graphical representation of absorber height versus temperature illustrates the temperature profiles in the gas and liquid phase. Providing the loading factor profile is especially important for absorption processes with a pronounced temperature bulge as shown in the first graphical representation. Such temperature bulge occurs when exothermic heat of reaction and/or heat of absorption is released. The second graphical representation of absorber height versus $CO_2$ concentration illustrates the $CO_2$ concentration profile in the gas phase.

Temperature and $CO_2$ concentration in the gas phase determine the equilibrium loading profile of $CO_2$ in the liquid phase as shown by the dashed line in the third graphical representation of absorber height versus $CO_2$ loading. The actual loading profile of $CO_2$ in the liquid phase as shown by the solid line is determined in for each iteration of the equation-based solution method. The loading factor profile as shown in the fourth graphical representation is defined by the actual loading of $CO_2$ in the liquid phase divided by the equilibrium loading.

A value of 1 for the loading factor means that the equilibrium value is reached and no mass transfer occurs. This will lead to an infinite absorber height as calculation result for specifying a $CO_2$ concentration in the treated outlet gas. As consequence, for designing gas treatment plants the loading factor needs to be specified to a value <1 to avoid a physically not possible specification. A reasonable loading factor is for instance <0.95 or <0.9.

If $CO_2$ and $H_2S$ both are present in the inlet gas the single loading factors of $CO_2$ or $H_2S$ may be misleading and may not be useful for specification. For such cases, a combined loading factor for $CO_2+H_2S$ is used as specification.

In the exemplary FIG. 6 of the loading factor profile along the absorber it can be observed that the maximum value of the loading factor is reached at the absorber top. This is due to specification of the $CO_2$ content in the treated gas at 90% of the absorber height and the available lean loading at the absorber top. This maximum loading factor at the absorber top is acceptable and does not lead to physically unreasonable conditions. However, the maximum loading factor around the position of the maximum temperature is critical and needs to be limited to values <1 as mentioned above. To ensure, that the maximum loading factor is specified at the right position, the loading factor is evaluated from absorber bottom to a defined absorber height fraction.

Figure 7:
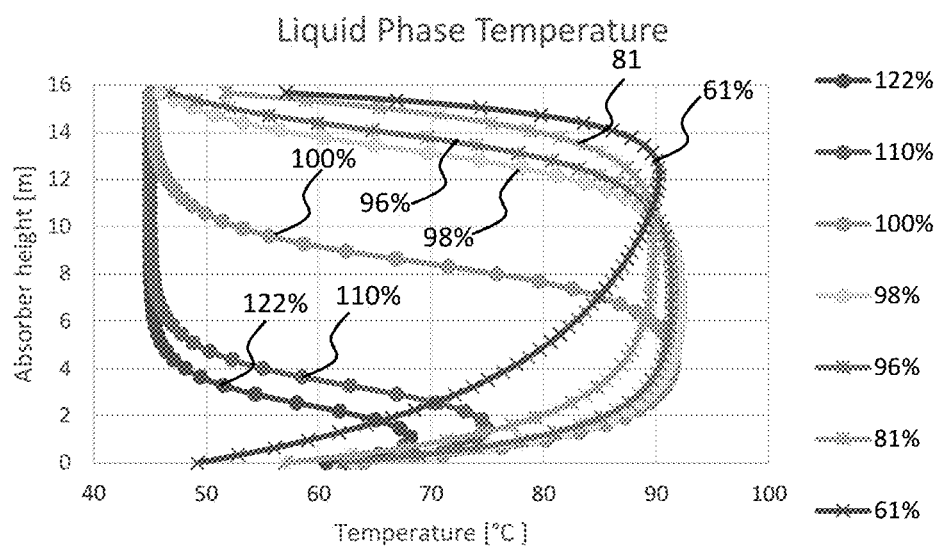
FIG. 7 shows the liquid phase temperature behavior illustrating absorber height versus temperature dependency for different flow rates.
Figure 8:
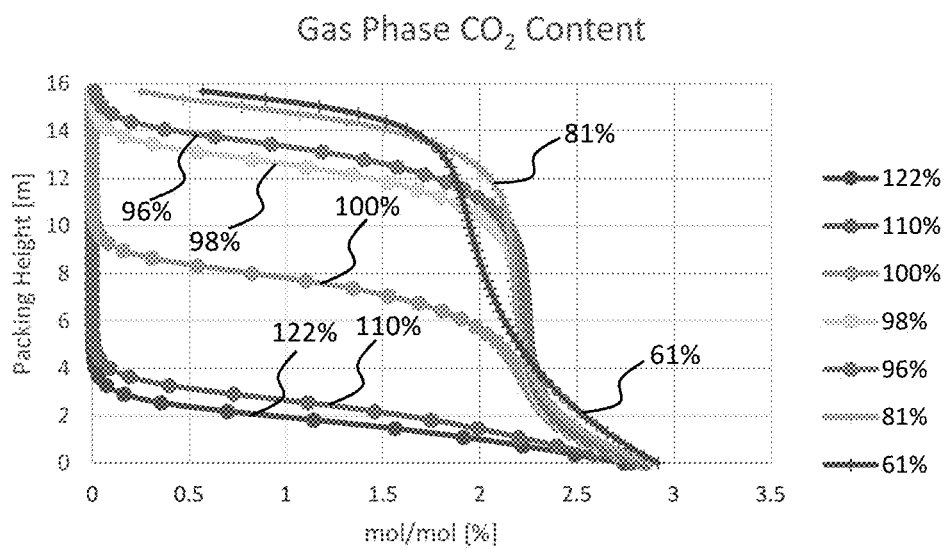
FIG. 8 shows the gas phase $CO_2$ content behavior illustrating absorber height versus $CO_2$ content dependency for different flow rates.
Figure 9:
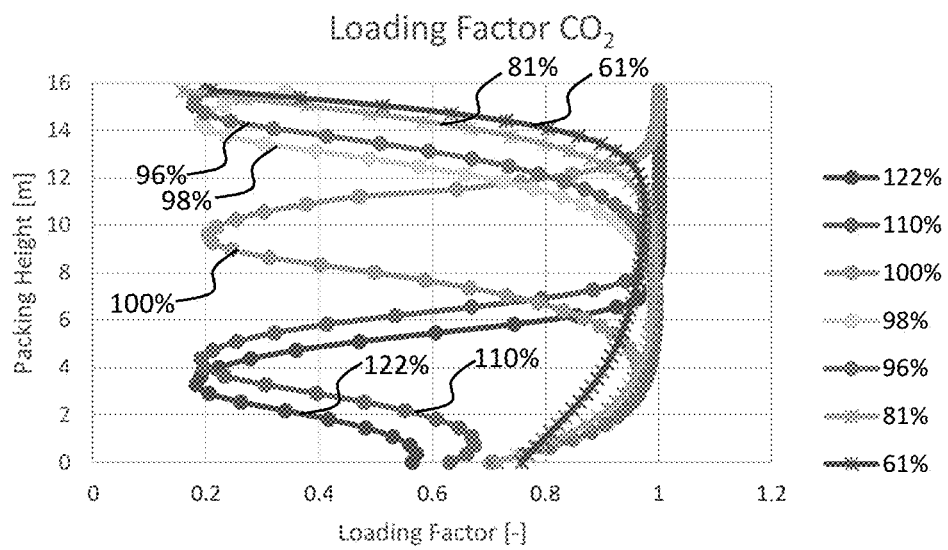
FIG. 9 shows the loading factor $CO_2$ behavior illustrating absorber height versus loading factor dependency for different flow rates.

FIGS. 7 to 9 illustrate the liquid phase temperature behavior, the gas phase CO2 content behavior and the loading factor as determined for different liquid flow rates in %. These illustrations resemble the behavior in the absorber of the gas treatment plant, if the liquid flow rate as parameter dependent on the plant throughput, is varied. Notably, the profiles in FIGS. 7 and 8 show a large effect in the profile shape for flow rates between 110% and 98%. Correspondingly, the concentration profile in FIG. 8. and the loading factor profile in FIG. 9 show that CO2 breakthrough occurs around 98% at the absorber top. Below and above the flow rate of 100% the profile shape does not change significantly. Hence around the flow rate of 100% the profile shapes are the most sensitive.

Figure 10:
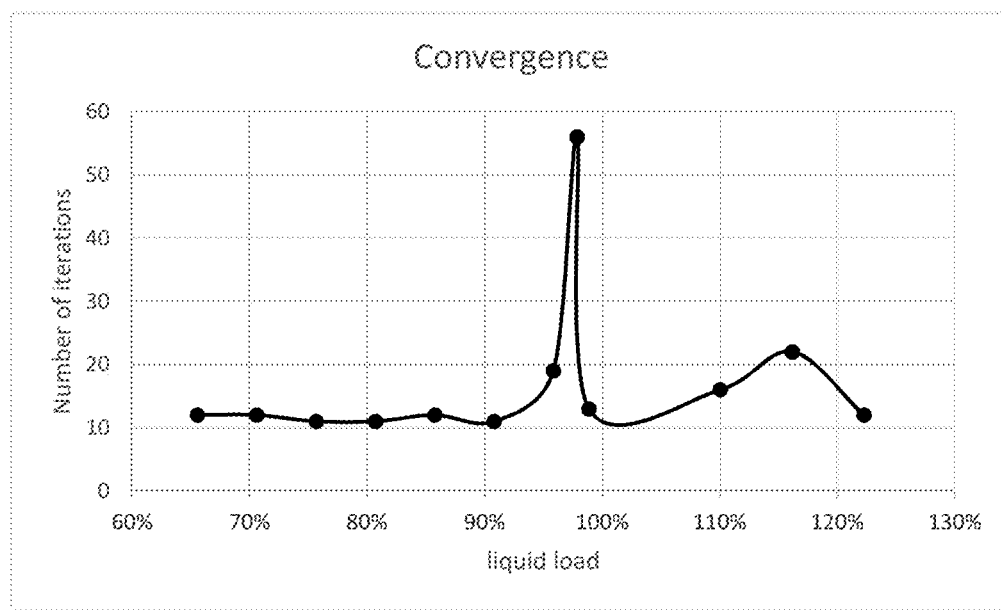
FIG. 10 shows the convergence behavior illustrating the number of iterations versus flow rate.

This behavior of the physical quantities in the absorber—temperature and CO2 content in the gas—is reflected in the number of iterations shown in FIG. 10 when stepwise increasing the flow rate for the given values. In the region between 96 to 98% flow rate the convergence behavior is such that the determination of operating and/or dimensioning parameters takes up to 6 times more iterations than above or below that region. For the operation of the absorber in the gas treatment plant this signifies an instable operation mode, since the absorber would be operated close to the CO2 gas breakthrough point. Hence, in setting the flow rate to an adequate value signifying a stable absorber operation is crucial to design a correspondingly stable gas treatment plant. In order to ensure that such a stable solution is provided in determining the operating and/or dimensioning parameters, it is highly advantageous to allow the loading factor as an input. Depending on whether the loading factor is determined at the absorber bottom or the maximum is taken along the absorber height, the two regimes where fast convergence is possible can be distinguished. At the same time such an approach ensures that the determination results in operating and/or dimensioning parameters that allow stable operation of the absorber and the gas treatment plant.

The following example illustrates the significant efficiency increase to a user for designing a gas treatment plant and the simplification of the design procedure. Given are the conditions of two different inlet gases referred to as Case A and Case B, which only differ in the concentration of carbon dioxide and methane. All other conditions like temperature, pressure flow rate and the concentration of residual components are identical. An overview of all inlet gas conditions is given in the following table:

| Feed gas conditions | Unit | Case A | Case B |
|---|---|---|---|
| Flow rate | Nm3/hr | 500000 | 500000 |
| Temperature | ° C. | 30 | 30 |
| Pressure | bar(a) | 60 | 60 |
| Composition in mole fraction | | | |
| Carbon dioxide ($CO_2$) | mole/mole | 0,5 | 10 |
| Methane ($CH_4$) | mole/mole | 93,5 | 84 |
| Ethane ($C_2H_6$) | mole/mole | 3 | 3 |
| Propane ($C_3H_8$) | mole/mole | 2 | 2 |
| Butane ($C_4H_{10}$) | mole/mole | 1 | 1 |
| Water content | — | saturated | saturated |

The task is to design a grassroots $CO_2$ removal plant for a LNG production plant with a $CO_2$ concentration in the treated gas of 50 mole-ppm. The plant configuration should consist of an absorption column, an HP flash and a regenerator column. The user needs to define several process parameters like solution flow rate, absorber height, absorber diameter, reboiler duty, and regenerator diameter.

Applying a state of the art process flow sheet simulator, plant geometry, conditions of inlet streams and process conditions need to be defined prior to running the simulation. The conditions of all outlet streams, like the $CO_2$ concentration in the treated gas, are a result of the calculation of the process simulator. For achieving a specified acid gas concentration in the treated gas, the user needs to change process conditions mentioned above in a lot of manual iterations until the required $CO_2$ concentration in the treated gas is reached. Reason is that even an experienced user a priori does not know the exact result for the operating and dimensioning parameters. Furthermore, the user may even define conditions during the manual iterations, which cannot lead to the required $CO_2$ concentration in the treated gas. As example, the required $CO_2$ concentration in the treated gas can only be reached, if the $CO_2$ concentration in the lean solution is below the corresponding $CO_2$ equilibrium concentration at the absorber top. Such conditions need to be identified by the user, which requires additional manual iterations.

In this example, the user needs to define not only but at least the five main process parameters solution flow rate, absorber height, absorber diameter, reboiler duty and regenerator diameter. The following table shows results for these five process parameters as relative values between the exemplary cases A and B.

| Main process parameters | Case A | Case B |
|---|---|---|
| Solution flow rate | P1 | 16,35 * P1 |
| Absorber packing height | P2 | 0,80 * P2 |
| Absorber diameter | P3 | 1,55 * P3 |
| Reboiler duty | P4 | 19,22 * P4 |
| Regenerator diameter | P5 | 4,27 * P5 |

Applying a state of the art process flow sheet simulator, the user requires a lot of manual iterations for the design of a $CO_2$ removal plant for Case A. Although knowing the result of Case A, Case B leads to very different conditions, which are not obvious to the user a priory. Thus, the user again requires a lot of manual iterations for the design of a $CO_2$ removal plant for Case B. These examples show, that application of a state of the art process simulator leads to a lot of manual and time-consuming iteration steps, which make the design process very tedious and inefficient.

Applying the present invention for the exemplary cases A and B and specifying the five parameters $CO_2$ concentration in the treated gas, maximum loading factor for $CO_2$ in the absorber, safety factor for the absorber, loading factor for $CO_2$ at the absorber top and safety factor for the regenerator, the user will receive the results shown in the table above in one step of manual input. This leads to a significant simplification of the design procedure and to a reduced time for the design procedure and thus to increased efficiency.

Any of the components described herein used for implementing the methods described herein may be in a form of a computer system having one or more processing devices capable of executing computer instructions. The computer system may be communicatively coupled (e.g., networked) to other machines in a local area network, an intranet, an extranet, or the Internet. The computer system may operate in the capacity of a server or a client machine in client-server network environment, or as a peer machine in a peer-to-peer (or distributed) network environment. The computer system may be a PC (Personal Computer), a tablet PC, a PDA (Personal Digital Assistant), a cellular telephone, a web appliance, a server, a network router, switch or bridge, or any machine capable of executing a set of instructions (sequential or otherwise) that specify actions to be taken by that machine. Further, it is to be understood that the terms "computer system," "machine," "electronic circuitry," and the like are not necessarily limited to a single component, and shall be taken to include any collection of machines that individually or jointly execute a set (or multiple sets) of instructions to perform any one or more of the methodologies discussed herein.

Some or all of the components of such a computer system may be utilized by or illustrative of any of the components of the system 100, such as the client device 110, the database 120, and the determination server 130. In some embodiments, one or more of these components may be distributed among multiple devices, or may be consolidated into fewer devices than illustrated. The computer system may include, for example, one or more processing devices, a main memory (e.g., ROM, flash memory, DRAM (Dynamic Random Access Memory) such as SDRAM (Synchronous DRAM) or RDRAM (Rambus DRAM), etc.), a static memory (e.g., flash memory, SRAM (Static Random Access Memory), etc.), and/or a data storage device, which communicate with each other via a bus.

A processing device may be a general-purpose processing device such as a microprocessor, microcontroller, central processing unit, or the like. More particularly, the processing device may be a CISC (Complex Instruction Set Computing) microprocessor, RISC (Reduced Instruction Set Computing) microprocessor, VLIW (Very Long Instruction Word) microprocessor, or a processor implementing other instruction sets or processors implementing a combination of instruction sets. The processing device may also be one or more special-purpose processing devices such as an ASIC (Application-Specific Integrated Circuit), an FPGA (Field Programmable Gate Array), a CPLD (Complex Programmable Logic Device), a DSP (Digital Signal Processor), a network processor, or the like. The methods, systems and devices described herein may be implemented as software in a DSP, in a micro-controller, or in any other side-processor or as hardware circuit within an ASIC, CPLD, or FPGA. It is to be understood that the term "processing device" may also refer to one or more processing devices, such as a distributed system of processing devices located across multiple computer systems (e.g., cloud computing), and is not limited to a single device unless otherwise specified.

The computer system may further include a network interface device. The computer system also may include a video display unit (e.g., an LCD (Liquid Crystal Display), a CRT (Cathode Ray Tube) display, or a touch screen), an alphanumeric input device (e.g., a keyboard), a cursor control device (e.g., a mouse), and/or a signal generation device (e.g., a speaker).

A suitable data storage device may include a computer-readable storage medium on which is stored one or more sets of instructions (e.g., software) embodying any one or more of the methodologies or functions described herein. The instructions may also reside, completely or at least partially, within the main memory and/or within the processor during execution thereof by the computer system, main memory, and processing device, which may constitute computer-readable storage media. The instructions may further be transmitted or received over a network via a network interface device.

A computer program for implementing one or more of the embodiments described herein may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network.

According to a further exemplary embodiment of the present invention, a data carrier or a data storage medium for making a computer program element available for downloading is provided, which computer program element is arranged to perform a method according to one of the previously described embodiments of the invention.

The terms "computer-readable storage medium," "machine-readable storage medium," and the like should be taken to include a single medium or multiple media (e.g., a centralized or distributed database, and/or associated caches and servers) that store the one or more sets of instructions. The terms "computer-readable storage medium," "machine-readable storage medium," and the like shall also be taken to include any transitory or non-transitory medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "receiving," "retrieving," "transmitting," "computing," "generating," "adding," "subtracting," "multiplying," "dividing," "selecting," "optimizing," "calibrating," "detecting," "storing," "performing," "analyzing," "determining," "enabling," "identifying," "modifying," "transforming," "applying," "extracting," and the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

It has to be noted that embodiments of the invention are described with reference to different subject matters. In particular, some embodiments are described with reference to method type claims whereas other embodiments are described with reference to the device type claims.

However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In some instances, well-known structures and devices are shown in block diagram form, rather than in detail, in order to avoid obscuring the present disclosure.

In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A method for determination of operating and/or dimensioning parameters of a gas treatment plant for treating a gaseous inlet stream with a treatment solution to provide a treated outlet stream including one or more gas treatment units, the method comprising:
   receiving, by a processing device, a request to initiate the determination of the operating and/or dimensioning parameters of the gas treatment plant, wherein the request comprises gas treatment unit input parameters for the one or more gas treatment units, wherein the gas treatment unit input parameters include at least one relative parameter that is not a temperature and that is not directly correlated to plant throughput of the gas treatment plant;
   initializing, by the processing device, a digital model of the gas treatment plant based on the gas treatment unit input parameters, wherein the digital model includes a relation of the at least one relative parameter to a correlated parameter, wherein the correlated parameter is dependent on the plant throughput or representative of a gas treatment unit geometry and is a result of the relation to the at least one relative parameter, and wherein the digital model characterizes mass and heat transfer in the gas treatment plant including the one or more gas treatment units;
   determining, by the processing device, the operating and/or dimensioning parameters of the gas treatment plant including the correlated parameter based on the digital model; and
   outputting, by the processing device, the operating and/or dimensioning parameters including the correlated parameter dependent on the plant throughput or dependent on the gas treatment unit geometry.

2. The method of claim 1, wherein one of the one or more gas treatment units is an absorber, wherein absorber input parameters are received which include at least one of the following relative parameters:
   i. a composition specifying a proportion of one or more depleted gas component(s) in the treated outlet stream,
   ii. a loading factor indicating a distance to an equilibrium capture capacity of the treatment solution in the absorber, or
   iii. an acceptable hydraulic load indicating an acceptable hydraulic operational regime in the absorber.

3. The method of claim 2, wherein the absorber input parameters include the loading factor, which is related to an actual loading and an equilibrium loading.

4. The method of claim 2, wherein the absorber input parameters include the loading factor, which is determined by an extremum of a ratio of actual loading to equilibrium loading or vice versa along height of the absorber or at a bottom of the absorber.

5. The method of claim 2, wherein the loading factor of the treatment solution is determined based on one or more gas component(s) to be absorbed from the gaseous inlet stream, wherein in case of more than one gas component to be absorbed from the gaseous inlet stream, the loading factor is determined as combined loading factor including the more than one gas components to be absorbed.

6. The method of claim 1, wherein one of the one or more gas treatment units includes a regenerator, which comprises at least one reboiler for regenerating the treatment solution and feeding the regenerated treatment solution back into an absorber, wherein the request further comprises regenerator input parameters including at least one of the following relative parameters:
   i. a fraction quality of the regenerated treatment solution, a strip steam ratio, or a loading factor indicating a distance to an equilibrium capture capacity of the regenerated treatment solution at a top of the absorber, or
   ii. an acceptable hydraulic load indicating an acceptable hydraulic operational regime in the regenerator.

7. The method of claim 1, wherein the determining of the operating and/or dimensioning parameters includes using an equation-based solution method or a sequential solution method for the digital model.

8. The method of claim 7, wherein the equation-based solution method includes all equations of the digital model in a single system of equations, which are solved simultaneously.

9. The method of claim 1, wherein the request to initiate the determination of the operating and/or dimensioning parameters of the gas treatment plant is received from a client device, wherein the client device comprises a input unit, wherein an interface unit is part of a determination server associated with the processing device or the input unit and the interface unit are part of the client device, and wherein the gas treatment unit input parameters are provided according to one or more permissions that define which gas treatment unit input parameters are provided as a relative parameter or as a correlated parameter.

10. The method of claim 1, wherein for the initializing of the digital model, thermodynamic parameters are provided via a database unit, wherein the thermodynamic parameters are derived from measurements of thermodynamic properties of gas treatment plants under operating conditions.

11. The method of claim 1, wherein a validation step is performed for the at least one relative parameter before and/or after receipt of the request, wherein the at least one relative parameter is valid responsive to the at least one relative parameter being within a pre-defined range.

12. A system for determination of operating and/or dimensioning parameters of a gas treatment plant for treating a gaseous inlet stream with a treatment solution to provide a treated outlet stream including one or more gas treatment units, the system comprising:
   a determination server communicatively coupled to a client device and a database server comprising a database, wherein the determination server is configured to:
      receive a request to initiate the determination of the operating and/or dimensioning parameters of the gas treatment plant, wherein the request comprises gas treatment unit input parameters for the one or more gas treatment units, wherein the gas treatment unit input parameters include at least one relative parameter that is not a temperature and that is not directly correlated to plant throughput of the gas treatment plant;
      initialize a digital model of the gas treatment plant based on the gas treatment unit input parameters, wherein the digital model includes a relation of the at least one relative parameter to a correlated parameter, wherein the correlated parameter is dependent on the plant throughput or representative of a gas treatment unit geometry and is a result of the relation to the at least one relative parameter, and wherein the digital model characterizes mass and heat transfer in the gas treatment plant including the one or more gas treatment units;
      determine the operating and/or dimensioning parameters of the gas treatment plant including the correlated parameter based on the digital model; and
      output the operating and/or dimensioning parameters including the correlated parameter dependent on the plant throughput or dependent on the gas treatment unit geometry.

13. The system of claim 12, wherein one of the one or more gas treatment units is an absorber, wherein absorber input parameters are received which include at least one of the following relative parameters:
   i. a composition specifying a proportion of one or more depleted gas component(s) in the treated outlet stream,
   ii. a loading factor indicating a distance to an equilibrium capture capacity of the treatment solution in the absorber, or
   iii. an acceptable hydraulic load indicating an acceptable hydraulic operational regime in the absorber.

14. The system of claim 13, wherein the absorber input parameters include the loading factor, which is related to an actual loading and an equilibrium loading.

15. The system of claim 13, wherein the absorber input parameters include the loading factor, which is determined by an extremum of a ratio of actual loading to equilibrium loading or vice versa along height of the absorber or at a bottom of the absorber.

16. A non-transitory computer-readable storage medium having instructions encoded thereon that, when executed by a processing device, configure the processing device to:
   receive a request to initiate determination of operating and/or dimensioning parameters of a gas treatment plant, wherein the request comprises gas treatment unit input parameters for one or more gas treatment units, wherein the gas treatment unit input parameters include at least one relative parameter that is not a temperature and that is not directly correlated to plant throughput of the gas treatment plant;
   initialize a digital model of the gas treatment plant based on the gas treatment unit input parameters, wherein the digital model includes a relation of the at least one relative parameter to a correlated parameter, wherein the correlated parameter is dependent on the plant throughput or representative of gas treatment unit geometry and is a result of the relation to the at least one relative parameter, and wherein the digital model characterizes mass and heat transfer in the gas treatment plant including the one or more gas treatment units;
   determine the operating and/or dimensioning parameters of the gas treatment plant including the correlated parameter based on the digital model; and
   output the operating and/or dimensioning parameters including the correlated parameter dependent on the plant throughput or dependent on the gas treatment unit geometry.

17. The non-transitory computer-readable storage medium of claim 16, wherein one of the one or more gas treatment units is an absorber, wherein absorber input parameters are received which include at least one of the following relative parameters:
   i. a composition specifying a proportion of one or more depleted gas component(s) in a treated outlet stream provided by treating a gaseous inlet stream with a treatment solution,
   ii. a loading factor indicating a distance to an equilibrium capture capacity of the treatment solution in the absorber, or
   iii. an acceptable hydraulic load indicating an acceptable hydraulic operational regime in the absorber.

18. The non-transitory computer-readable storage medium of claim 17, wherein the absorber input parameters include the loading factor, which is related to an actual loading and an equilibrium loading.

19. The non-transitory computer-readable storage medium of claim 17, wherein the absorber input parameters include the loading factor, which is determined by an extremum of a ratio of actual loading to equilibrium loading or vice versa along height of the absorber or at a bottom of the absorber.

20. The method of claim 1, wherein the correlated parameter is representative of the gas treatment unit geometry.

* * * * *